United States Patent
Uemori et al.

(10) Patent No.: US 10,609,354 B2
(45) Date of Patent: Mar. 31, 2020

(54) MEDICAL IMAGE PROCESSING DEVICE, SYSTEM, METHOD, AND PROGRAM

(71) Applicant: SONY CORPORATION, Tokyo (JP)

(72) Inventors: Takeshi Uemori, Tokyo (JP); Tsuneo Hayashi, Tokyo (JP); Kenji Takahasi, Kanagawa (JP); Yuki Sugie, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 15 days.

(21) Appl. No.: 16/072,241

(22) PCT Filed: Nov. 15, 2016

(86) PCT No.: PCT/JP2016/083868
§ 371 (c)(1),
(2) Date: Jul. 24, 2018

(87) PCT Pub. No.: WO2017/138209
PCT Pub. Date: Aug. 17, 2017

(65) Prior Publication Data
US 2019/0037202 A1 Jan. 31, 2019

(30) Foreign Application Priority Data
Feb. 12, 2016 (JP) ................................. 2016-024865

(51) Int. Cl.
*H04N 13/128* (2018.01)
*A61B 90/20* (2016.01)
(Continued)

(52) U.S. Cl.
CPC ....... *H04N 13/128* (2018.05); *A61B 1/00006* (2013.01); *A61B 1/00009* (2013.01);
(Continued)

(58) Field of Classification Search
CPC .. H04N 13/128; G06T 7/593; A61B 1/00006; A61B 1/00193; A61B 1/3132
(Continued)

(56) References Cited

U.S. PATENT DOCUMENTS

2014/0139526 A1* 5/2014 Kim .................... G06T 7/0012
345/424
2015/0350632 A1* 12/2015 Chang .................. H04N 13/128
348/54

FOREIGN PATENT DOCUMENTS

| JP | 2011-250059 A | 12/2011 |
| JP | 2013-223666 A | 10/2013 |
| JP | 2014-175965 A | 9/2014 |

OTHER PUBLICATIONS

International Search Report dated Feb. 7, 2017, in PCT/JP2016/083868, filed Nov. 15, 2016.

* cited by examiner

Primary Examiner — Patricia I Young
(74) Attorney, Agent, or Firm — Xsensus LLP

(57) ABSTRACT

[Object] To make it possible to achieve a favorable disparity by setting an operation depth of medical operation as a target while reducing an influence of correction of a disparity for stereoscopic vision over accuracy of an image.
[Solution] There is provided a medical image processing device including: a depth determination unit configured to determine an operation depth of medical operation whose image is to be captured; a disparity determination unit configured to determine a disparity by using a captured image showing a visual field observed in the operation and generate disparity information; and a correction unit configured to correct the disparity information depending on the operation depth determined by the depth determination unit.

17 Claims, 23 Drawing Sheets

(51) Int. Cl.
| | | |
|---|---|---|
| *A61B 90/30* | (2016.01) | |
| *G06T 7/50* | (2017.01) | |
| *H04N 13/20* | (2018.01) | |
| *A61B 1/00* | (2006.01) | |
| *A61B 1/313* | (2006.01) | |
| *G02B 23/24* | (2006.01) | |
| *G03B 25/00* | (2006.01) | |
| *H04N 5/225* | (2006.01) | |
| *H04N 7/18* | (2006.01) | |
| *A61B 90/00* | (2016.01) | |
| *G03B 35/08* | (2006.01) | |
| *H04N 13/239* | (2018.01) | |
| *G06T 7/593* | (2017.01) | |
| *H04N 13/00* | (2018.01) | |
| *A61B 1/04* | (2006.01) | |

(52) U.S. Cl.
CPC ........ *A61B 1/00193* (2013.01); *A61B 1/3132* (2013.01); *A61B 90/20* (2016.02); *A61B 90/37* (2016.02); *G02B 23/2415* (2013.01); *G02B 23/2484* (2013.01); *G03B 35/08* (2013.01); *G06T 7/593* (2017.01); *H04N 5/225* (2013.01); *H04N 7/18* (2013.01); *H04N 13/239* (2018.05); *A61B 1/00045* (2013.01); *A61B 1/00149* (2013.01); *A61B 1/042* (2013.01); *A61B 2090/371* (2016.02); *G06T 2207/10028* (2013.01); *G06T 2207/10068* (2013.01); *G06T 2207/20228* (2013.01); *G06T 2207/30004* (2013.01); *H04N 2013/0081* (2013.01)

(58) Field of Classification Search
USPC .......................................................... 348/42
See application file for complete search history.

AT TIME OF CAPTURING IMAGE OF RIGHT EYE

AT TIME OF CAPTURING IMAGE OF LEFT EYE

MEDICAL IMAGE PROCESSING DEVICE, SYSTEM, METHOD, AND PROGRAM

TECHNICAL FIELD

The present disclosure relates to a medical image processing device, system, method, and program.

BACKGROUND ART

Conventionally, in order to stereoscopically display an image showing a real space, there has been used a method of determining a disparity between two captured images from a stereo camera and generating a stereoscopic image by using the determined disparity. For example, Patent Literature 1 cited below discloses a technology of converting a disparity determined by using captured images so as to emphasize a stereoscopic effect of a main subject and then performing stereoscopic display.

CITATION LIST

Patent Literature

Patent Literature 1: JP 2011-250059A

DISCLOSURE OF INVENTION

Technical Problem

However, correction of a stereoscopic effect of a stereoscopic image based on correction of a disparity causes a defect of a pixel caused by a shift of a subject in the image. Even if a pixel value of the defective pixel is interpolated on the basis of adjacent pixels, an image displayed as described above does not accurately reflect a situation of a real world. In particular, in a medical scene such as surgery or diagnosis, it is desirable to avoid display of an inaccurate image as much as possible.

Solution to Problem

According to the present disclosure, there is provided a medical image processing device including: a depth determination unit configured to determine an operation depth of medical operation whose image is to be captured; a disparity determination unit configured to determine a disparity by using a captured image showing a visual field observed in the operation and generate disparity information; and a correction unit configured to correct the disparity information depending on the operation depth determined by the depth determination unit.

In addition, according to the present disclosure, there is provided a medical image processing system including: the above-described medical image processing device; and an imaging device configured to capture an image of the visual field and generate the captured image.

In addition, according to the present disclosure, there is provided an image processing method executed by a medical image processing device, the image processing method including: determining an operation depth of medical operation whose image is to be captured; determining a disparity by using a captured image showing a visual field observed in the operation and generating disparity information; and correcting the disparity information depending on the determined operation depth.

In addition, according to the present disclosure, there is provided a program for causing a processor that controls a medical image processing device to function as: a depth determination unit configured to determine an operation depth of medical operation whose image is to be captured; a disparity determination unit configured to determine a disparity by using a captured image showing a visual field observed in the operation and generate disparity information; and a correction unit configured to correct the disparity information depending on the operation depth determined by the depth determination unit.

Advantageous Effects of Invention

According to a technology of the present disclosure, it is possible to achieve a favorable disparity by setting an operation depth of medical operation as a target while reducing an influence of correction of a disparity for stereoscopic vision over accuracy of an image.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
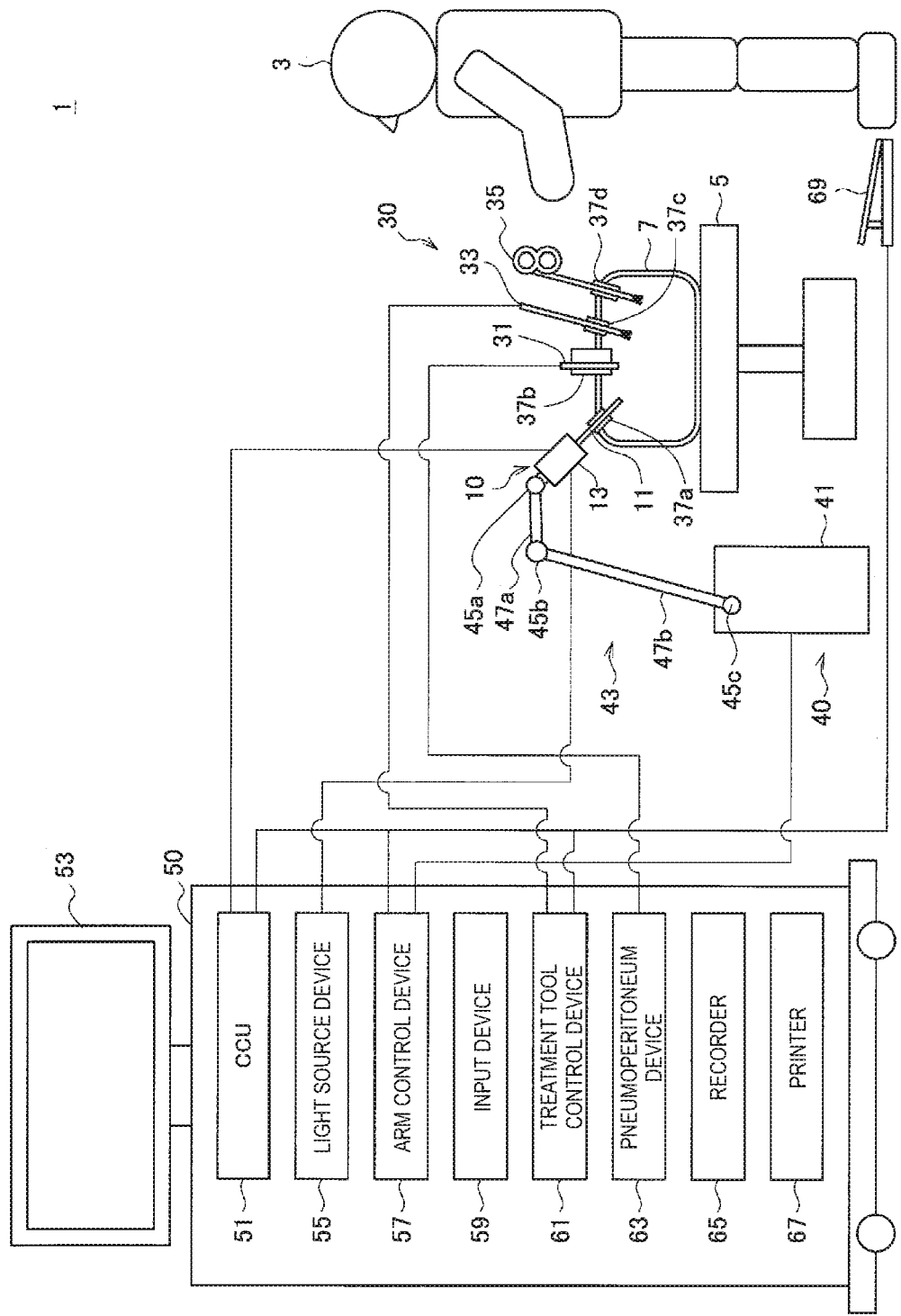
FIG. 1 is an explanatory diagram for describing a schematic configuration of a medical image processing system according to an embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, description will be provided in the following order.
1. Introduction
1-1. Overview of system
1-2. Description of problem
2 First embodiment
2-1. Configuration example of image processing device
2-2. Flow of processing
3. Second embodiment
3-1. Configuration example of image processing device
3-2. Flow of processing
4. Third embodiment
4-1. Configuration example of image processing device
4-2. Flow of processing
5. Reduction in stereoscopic effect
6. Conclusion 1. Introduction

[1-1. Overview of System]

In this section, an overview of an example system to which a technology according to the present disclosure is applicable will be described. FIG. 1 illustrates an example of a schematic configuration of a medical image processing system 1 according to an embodiment. The medical image processing system 1 is an endoscopic surgery system. In the example of FIG. 1, a practitioner (doctor) 3 performs endoscopic surgery by using the medical image processing system 1 on a patient 7 on a patient bed 5. The medical image processing system 1 includes an endoscope 10, other surgical instruments (operation instruments) 30, a support arm device 40 that supports the endoscope 10, and a cart 50 on which various devices for endoscopic surgery are mounted.

In endoscopic surgery, an abdominal wall is punctured with a plurality of cylindrical opening tools 37a to 37d called trocars, instead of being cut to open an abdomen. Then, a lens barrel 11 of the endoscope 10 and the other operation instruments 30 are inserted into a body cavity of the patient 7 through the trocars 37a to 37d. In the example of FIG. 1, a pneumoperitoneum tube 31, an energy treatment device 33, and a forceps 35 are illustrated as the other operation instruments 30. The energy treatment device 33 is used for treatment such as incision or separation of tissue or sealing of a blood vessel with a high-frequency current or ultrasonic vibration. Note that the illustrated operation instruments 30 are merely examples, and other types of operation instruments (e.g., thumb forceps, retractor, or the like) may be used.

An image of the inside of the body cavity of the patient 7 captured by the endoscope 10 is displayed by a display device 53. The practitioner 3 performs, for example, treatment such as excision of an affected part by using the energy treatment device 33 and the forceps 35 while viewing the display image in real time. Note that, although not illustrated, the pneumoperitoneum tube 31, the energy treatment device 33, and the forceps 35 are supported by a user such as the practitioner 3 or an assistant during surgery.

The support arm device 40 includes an arm portion 43 extending from a base portion 41. In the example of FIG. 1, the arm portion 43 includes joint portions 45a, 45b, and 45c and links 47a and 47b and supports the endoscope 10. As a result of driving the arm portion 43 under the control of an arm control device 57, a position and posture of the endoscope 10 can be controlled, and fixation of a stable position of the endoscope 10 can also be achieved.

The endoscope 10 includes the lens barrel 11 and a camera head 13 connected to a base end of the lens barrel 11. Part of the lens barrel 11, which has a certain length from a tip thereof, is inserted into the body cavity of the patient 7. In the example of FIG. 1, the endoscope 10 is configured as a so-called rigid endoscope having a rigid lens barrel 11. However, the endoscope 10 may be configured as a so-called flexible endoscope.

An opening into which an objective lens is fit is provided at the tip of the lens barrel 11. A light source device 55 is connected to the endoscope 10, and light generated by the light source device 55 is guided to the tip of the lens barrel by a light guide extended in the lens barrel 11, and an observation target in the body cavity of the patient 7 is irradiated with the light via the objective lens. Note that the endoscope 10 may be a forward-viewing endoscope, a forward-oblique viewing endoscope, or a lateral-viewing endoscope.

The camera head 13 is an imaging device including an optical system, a drive system, and an image sensor. The optical system typically includes a lens unit and collects observation light (reflected light of irradiation light) from a subject, the observation light being taken in through the tip of the lens barrel 11, toward the image sensor. Positions of a zoom lens and a focus lens in the lens unit are changeable by being driven by the drive system in order to variably control imaging conditions such as a magnification and a focal distance. The image sensor of the camera head 13 performs photoelectric conversion on the observation light collected by the optical system and generates an image signal serving as an electric signal. The image sensor may be a 3CCD sensor including individual imaging elements that generate image signals of respective three color components or may be another type of image sensor such as a 1CCD image sensor or a 2CCD image sensor. The image sensor may include, for example, any type of imaging element such as a complementary metal oxide semiconductor (CMOS) or a charge-coupled device (CCD). The image signals generated by the image sensor are transmitted as RAW data to a camera control unit (CCU) 51. In an embodiment, a captured image shown by the image signals generated by the camera head 13 includes a right-eye image and a left-eye image for stereoscopic vision. The right-eye image and the left-eye image may be generated by a right-eye image sensor and a left-eye image sensor of a compound-eye camera, respectively. Instead of this, the right-eye image and the left-eye image may be generated by a single image sensor of a monocular camera (e.g., by a shutter switching method).

The CCU 51 is connected to the camera head 13 via a signal line and a communication interface. The signal line between the camera head 13 and the CCU 51 is, for example, a high-speed transmission line capable of enabling bidirectional communication, such as an optical cable. The CCU 51 includes a processor such as a central processing unit (CPU) and a memory such as a random access memory (RAM) and comprehensively controls operation of the endoscope 10 and the display device 53. The CCU 51 may further include a frame memory for temporarily storing image signals and one or more graphics processing units (GPUs) that execute image processing. For example, the CCU 51 generates a stereoscopic image on the basis of the captured image input from the camera head 13 and causes the display device 53 to display the generated stereoscopic image. In an embodiment, the CCU 51 may generate a right-eye display image and a left-eye display image by processing the right-eye image and the left-eye image so as to emphasize a stereoscopic effect expressed by the stereoscopic image. In another embodiment, the CCU 51 may generate a right-eye display image and a left-eye display image by processing the right-eye image and the left-eye image so as to reduce a stereoscopic effect expressed by the stereoscopic image. Then, the CCU 51 outputs display image signals that show the right-eye display image and the left-eye display image to the display device 53. A series of display images can form a moving image (video). The image processing executed in the CCU 51 may include, for example, general processing such as development and noise reduction. Further, the CCU 51 transmits a control signal to the camera head 13 to control drive of the camera head 13. The control signal can include, for example, information that specifies the imaging conditions described above.

The display device 53 displays the stereoscopic image on the basis of the input display image signals under the control of the CCU 51. The display device 53 may display the stereoscopic image by any method such as an active shutter method, a passive method, or a glassless method.

The light source device 55 includes, for example, an LED, a xenon lamp, a laser light source, or a light source corresponding to a combination thereof and supplies irradiation light with which the observation target is to be irradiated to the endoscope 10 via the light guide.

The arm control device 57 includes, for example, a processor such as a CPU and operates in accordance with a predetermined program to control drive of the arm portion 43 of the support arm device 40.

An input device 59 includes one or more input interfaces that accept user input to the medical image processing system 1. The user can input various pieces of information or input various instructions to the medical image processing system 1 via the input device 59. For example, the user may input setting information or other parameters described below via the input device 59. Further, for example, the user inputs an instruction to drive the arm portion 43, an instruction to change the imaging conditions (the type of irradiation light, a magnification, a focal distance, and the like) in the endoscope 10, an instruction to drive the energy treatment device 33, or the like via the input device 59.

The input device 59 may treat any type of user input. For example, the input device 59 may detect physical user input via a mechanism such as a mouse, a keyboard, a switch (e.g., a foot switch 69), or a lever. The input device 59 may detect touch input via a touchscreen. The input device 59 may be achieved in the form of a wearable device such as an eyeglass-type device or a head mounted display (HMD) and may detect a line of sight or gesture of the user. Further, the input device 59 may include a microphone capable of acquiring voice of the user and may detect an audio command via the microphone.

A treatment tool control device 61 controls drive of the energy treatment device 33 for treatment such as cauterization or incision of tissue or sealing of a blood vessel. A pneumoperitoneum device 63 secures a visual field observed by using the endoscope 10 and sends gas into the body cavity via the pneumoperitoneum tube 31 in order to inflate the body cavity of the patient 7 for the purpose of securing an operational space of the practitioner. A recorder 65 records various pieces of information regarding medical operation (e.g., one or more of setting information, image information, and measurement information from a vital sensor (not illustrated)) on a recording medium. A printer 67 prints various pieces of information regarding medical operation in some format such as text, an image, or a graph.

[1-2. Description of Problem]

In such a medical image processing system, a base length between a right-eye image and a left-eye image is shorter than a base length in a non-medical stereo camera because a diameter of the camera head to be inserted into a body cavity of a patient is restricted. In addition, a disparity is smaller as the base length is shorter in a case where a depth of a subject is not changed. As a result, there is a possibility that a stereoscopic image displayed on the basis of the right-eye image and the left-eye image cannot give a sufficient stereoscopic effect to the user.

Figure 2A:
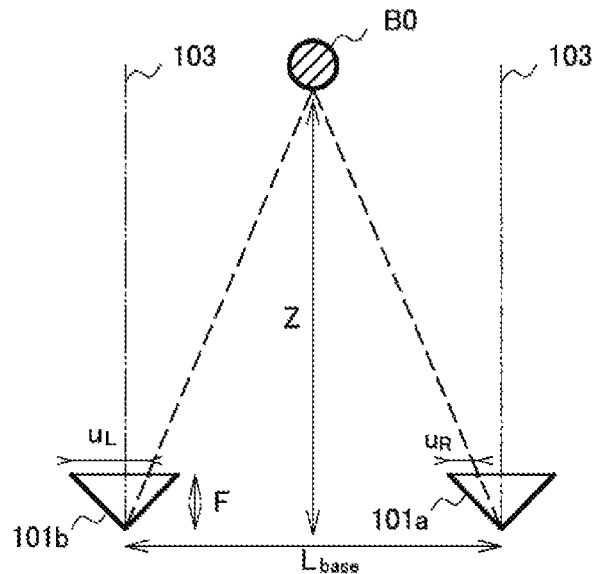
FIG. 2A is an explanatory diagram for describing a relationship among a base length, a depth of a subject, and a disparity in a compound-eye stereo camera.

FIG. 2A is an explanatory diagram for describing a relationship among a base length, a depth of a subject, and a disparity in a compound-eye stereo camera. When referring to FIG. 2A, a right-eye image sensor 101$a$ and a left-eye image sensor 101$b$ are each illustrated as an inverted triangle. An upper side of each inverted triangle corresponds to an imaging surface of the image sensor and a bottom vertex corresponds to a focal point. In FIG. 2A, F denotes a focal distance, and $L_{base}$ denotes a base length between the image sensors (e.g., a distance between two optical centers 103). In the example of FIG. 2A, a subject B0 exists at a position of a distance Z from the base line between the right-eye image sensor 101$a$ and the left-eye image sensor 101$b$. In the present specification, this distance Z will be referred to as "depth". The subject B0 appears at a horizontal position $u_R$ on the imaging surface of the right-eye image sensor 101$a$. Further, the subject B0 appears at a horizontal position $U_L$, on the imaging surface of the left-eye image sensor 101b. In a case where the use of a pinhole camera model is presupposed for simplicity of explanation, a disparity d based on the right-eye image sensor 101a is given by the following expression:

[Math. 1]

$$d = u_L u_R \quad (1)$$

Further, when the depth Z has a variable value, the disparity d(Z) serving as a function of the depth Z can be expressed by the following expression with the use of the base length $L_{base}$ and the focal distance F:

[Math. 2]

$$d(Z) = L_{base} \cdot \frac{F}{Z} \quad (2)$$

For example, the disparity d(Z) can be derived by a stereo matching method on the basis of the right-eye image and the left-eye image, and the depth Z of the subject can be calculated by using the derived disparity d(Z) and the already-known base length $L_{base}$ and focal distance F.

Figure 2B:
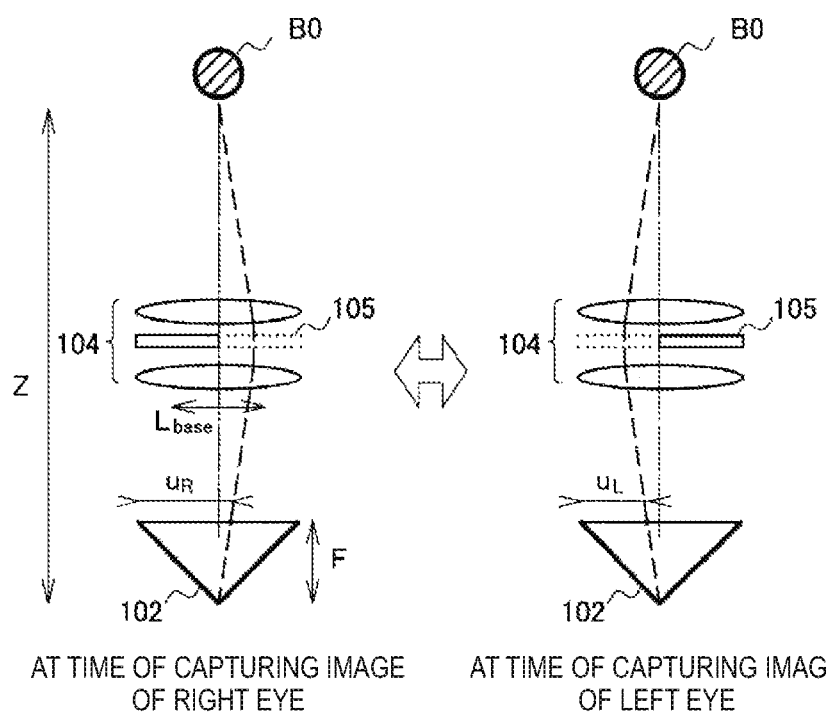
FIG. 2B is an explanatory diagram for describing a relationship among a base length, a depth of a subject, and a disparity in a monocular stereo camera.

FIG. 2B is an explanatory diagram for describing a relationship among a base length, a depth of a subject, and a disparity in a monocular stereo camera. When referring to FIG. 2B, a single image sensor 102 is illustrated as an inverted triangle. Further, not only a pair of lenses 104 but also a shutter 105 capable of selectively shielding a right half or a left half of the lenses is disposed in front of the image sensor 102. When an image of the right eye is captured, the shutter 105 shields the left half of the lenses and an image of observation light collected through the right half of the lenses is captured by the image sensor 102. When an image of the left eye is captured, the shutter 105 shields the right half of the lenses and an image of observation light collected through the left half of the lenses is captured by the image sensor 102. By capturing the images while temporally repeating such switching of the shutter, sequences of the right-eye image and the left-eye image are generated by the image sensor 102. The base length $L_{base}$ between the right-eye image and the left-eye image can be defined as, for example, a distance between a center of balance of the right half of a pupil (which corresponds to an image of a diaphragm of the optical system) at a position of the shutter 105 and a center of balance of the left half thereof. Also in the monocular stereo camera, the disparity d(Z) can be expressed by Expression (2) described above as the function of the depth Z of the subject by using the base length $L_{base}$ and the focal distance F.

Herein, a disparity (reference disparity) at a certain non-zero reference depth $Z_{ref}$ is denoted by $d_{ref}$, and a left side of Expression (2) is replaced with the sum of the reference disparity $d_{ref}$ and a residual d(Z) thereof. Then, the following expression is derived by moving a term of the reference disparity $d_{ref}$:

[Math. 3]

$$d(Z) = L_{base} \cdot \frac{F}{Z} - d_{ref} \quad (3)$$

Figure 3:
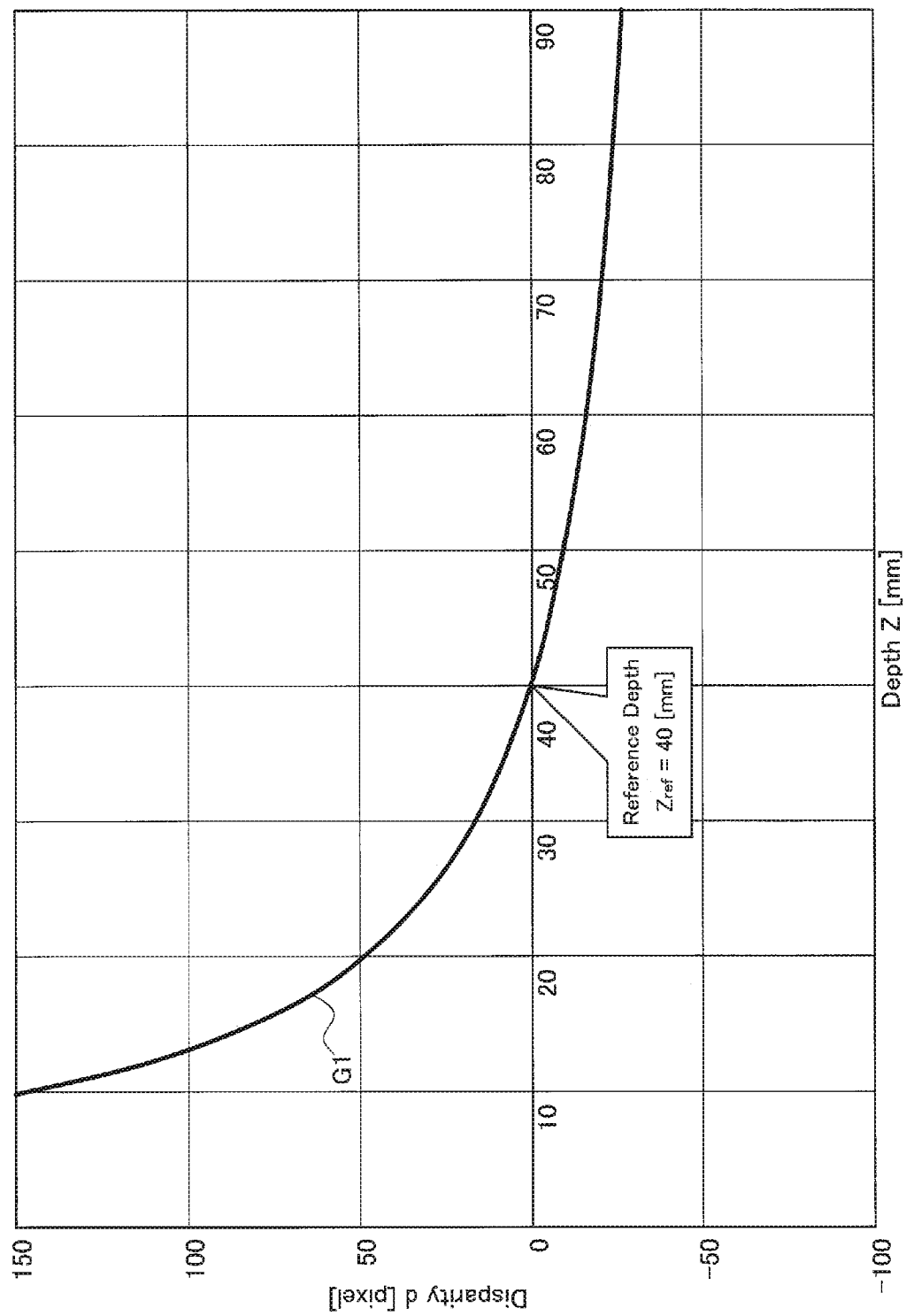
FIG. 3 is a graph showing an example of a relationship between a depth of a subject and a disparity.

In the following description, the residual d(Z) in Expression (3) will also be simply referred to as "disparity". FIG. 3 is a graph G1 showing an example of a relationship between the depth Z of the subject and the disparity d(Z) in a case of the reference depth $Z_{ref}$=40 mm. According to the graph G1, in a case where the depth Z is equal to the reference depth $Z_{ref}$, the disparity d(Z) is also equal to zero. The disparity d is increased to infinity as the depth Z is close to zero, whereas, when the depth Z is increased to exceed the reference depth $Z_{ref}$, the disparity d approaches $-d_{ref}$.

As described above, in the medical image processing system, the base length between the right-eye image and the left-eye image is restricted due to the diameter of the camera head, and therefore there is a possibility that a displayed stereoscopic image cannot give a sufficient stereoscopic effect to the user. In view of this, there is considered a method of artificially enlarging a disparity appearing in a captured right-eye image and left-eye image and then generating a stereoscopic image for the purpose of emphasizing the stereoscopic effect.

Figure 4:
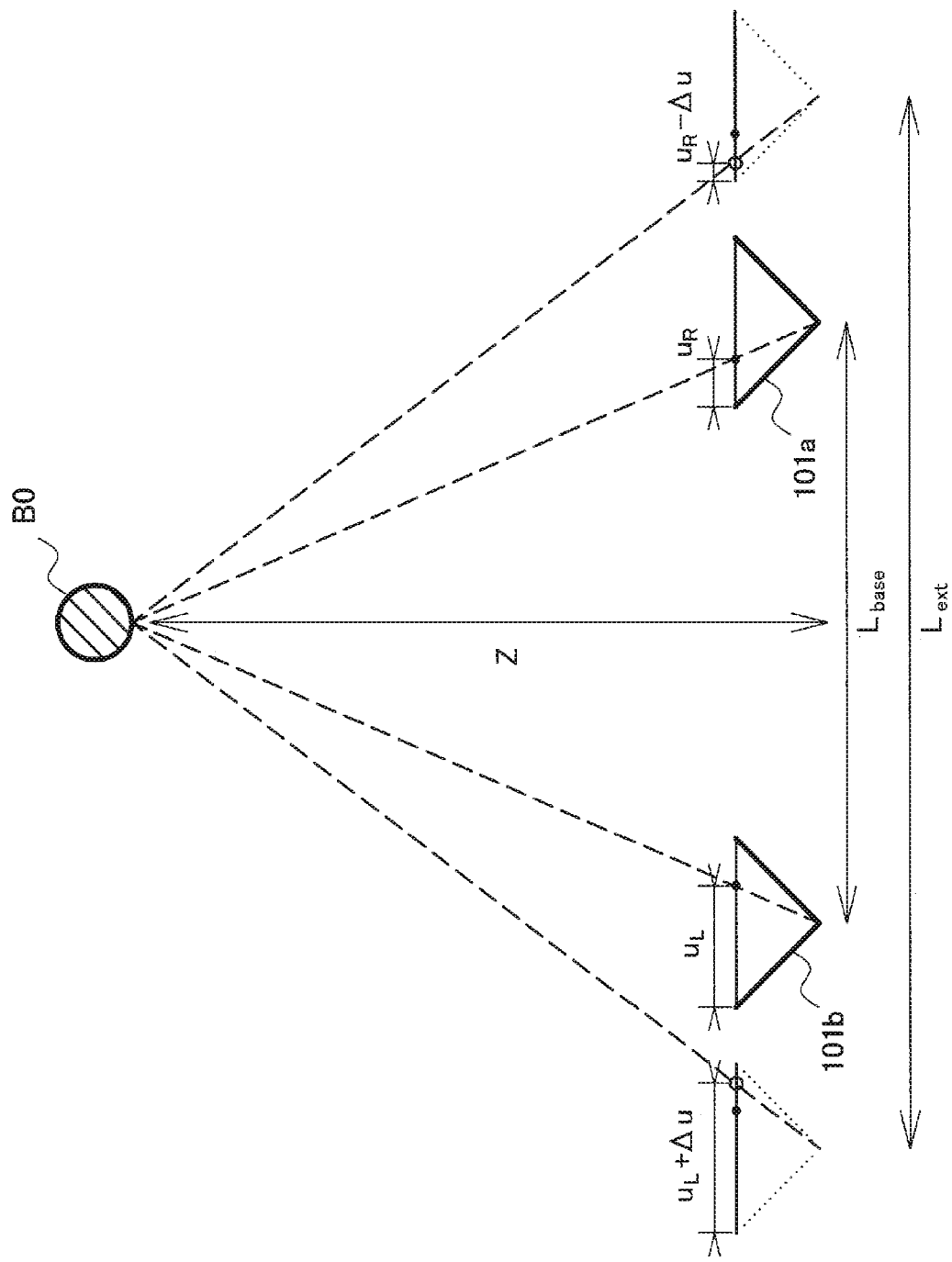
FIG. 4 is an explanatory diagram for describing emphasis of a stereoscopic effect obtained by correction of a disparity.

FIG. 4 is an explanatory diagram for describing emphasis of a stereoscopic effect obtained by correction of a disparity. FIG. 4 illustrates the right-eye image sensor 101a, the left-eye image sensor 101b, and the subject B0 illustrated in FIG. 2A again. An actual base length between the right-eye image sensor 101a and the left-eye image sensor 101b (hereinafter, referred to as "actual base length") is equal to $L_{base}$. Herein, the horizontal position $u_R$ of the subject B0 on the imaging surface of the right-eye image sensor 101a is shifted leftward by a value Δu ($u_R \rightarrow u_R - \Delta u$), and the horizontal position $u_L$, of the subject B0 on the imaging surface of the left-eye image sensor 101b is shifted rightward by the value Δu ($u_L \rightarrow u_L + \Delta u$), and therefore it is possible to simulatively achieve a stereoscopic effect similar to that of a stereoscopic image captured with a larger base length $L_{ext}$. Such shifts mean that the disparity d(Z) in Expression (3) is changed upward or downward. Note that the shift of the subject is not limited to the example of FIG. 4 and may be performed in only one of the right-eye image and the left-eye image. In this case, a shift amount can correspond to twice as much as a case where the subject is shifted in both the images.

Figure 5:
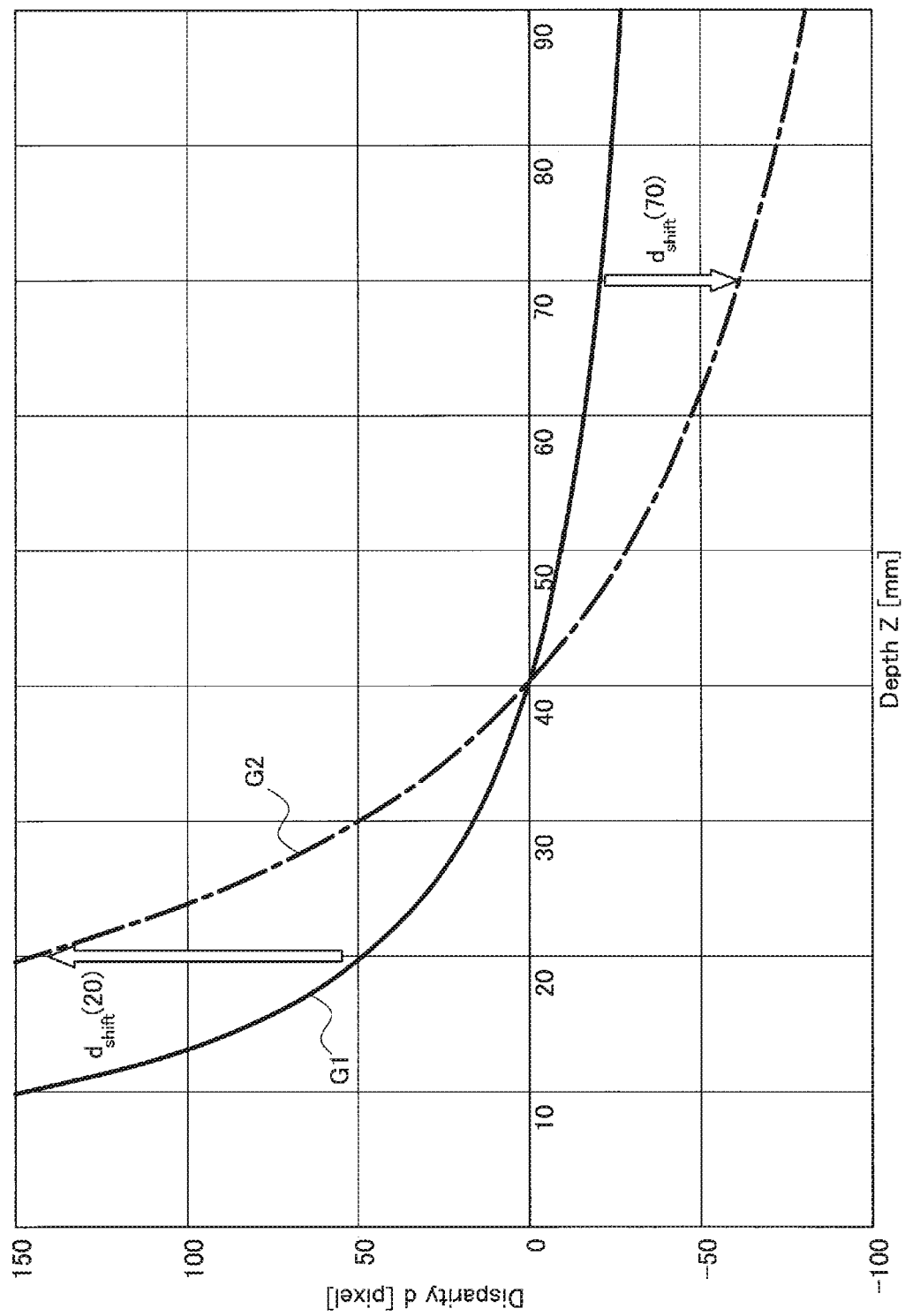
FIG. 5 is an explanatory diagram for describing correction of a disparity with a uniform correction factor.

As an example, a proportion for simulatively enlarging the base length $L_{base}$ is denoted by k. Herein, a base length of the endoscope for abdominal surgery is set to, for example, 0.7 mm. In a case of a correction factor k=3, the base length can be simulatively enlarged to have 2.1 mm by shifting the disparity, and, accordingly a stereoscopic effect of a stereoscopic image can be emphasized. FIG. 5 is an explanatory diagram for describing correction of a disparity with a uniform correction factor. A graph G2 shown in FIG. 5 is generated by enlarging the base length in a plot condition of the graph G1 shown in FIG. 3 to have a triple value. Also in the graph G2, in a case where the depth Z is equal to the reference depth $Z_{ref}$ (=40 mm), the disparity d(Z) is equal to zero. Note that, in the graph G2, the disparity d is increased at a faster pace than the pace in the graph G1 as the depth Z approaches zero. Further, when the depth Z is increased to exceed the reference depth $Z_{ref}$, the disparity d approaches a lower value than the value in the graph G1.

It is found from FIG. 5 that the shift amount necessary for emphasizing the stereoscopic effect of the right-eye image and the left-eye image captured by a camera having a base length=0.7 mm as if the right-eye image and the left-eye image are simulatively captured by a camera having a base length=2.1 mm (i.e., correction factor k=3) is, for example, $d_{shift}(20)$=approximately 95 pixels at the depth Z=20 mm and the shift amount $d_{shift}(70)$=approximately −40 pixels at the depth Z=70 mm, as shown by arrows in FIG. 5. Those shift amounts are especially larger than the shift amount needed in the vicinity of the reference depth. That is, emphasis of the stereoscopic effect using the uniform correction factor from the graph G1 to the graph G2 excessively increases a required shift amount within, in particular, a depth range far from the reference depth.

Figure 6:
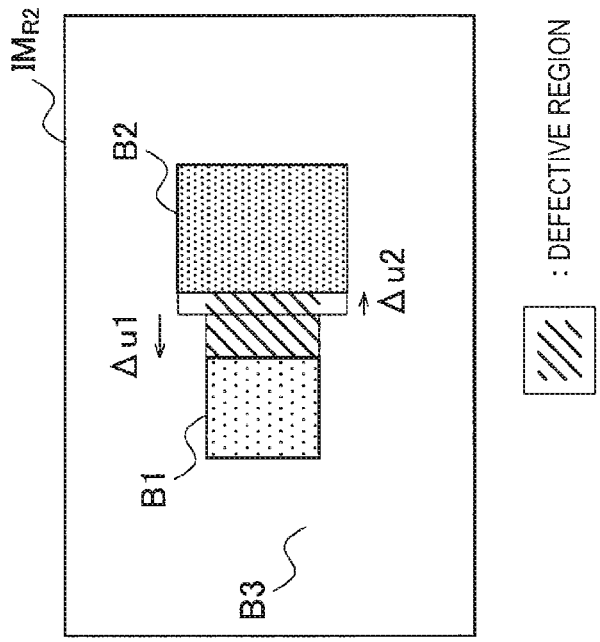
FIG. 6 is an explanatory diagram for describing a defect of pixels caused by correction of a disparity.
Figure 6:
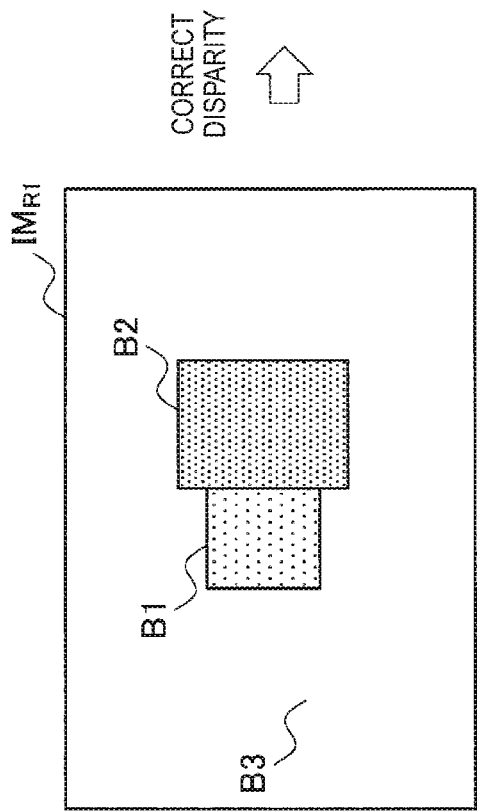

The shift of the subject for correcting the disparity for the purpose of emphasizing (or reducing) the stereoscopic effect causes a defect of pixels. FIG. 6 is an explanatory diagram for describing a defect of pixels caused by correction of the disparity. A left part of FIG. 6 illustrates a (uncorrected) right-eye image $IM_{R1}$ as an example generated by the image sensor. A first subject B1, a second subject B2, and a third subject B3 appear in the right-eye image $IM_{R1}$. Depths determined regarding those three subjects (e.g., as a result of matching with a left-eye image (not illustrated)) are different from one another. As an example, the first subject B1 exists at a depth shallower than the reference depth (i.e., has a depth smaller than the reference depth) and is shifted leftward by $\Delta u1$ in order to emphasize a stereoscopic effect. The second subject B2 exists at a depth deeper than the reference depth and is shifted rightward by $\Delta u2$ in order to emphasize a stereoscopic effect. As a result of such correction of the disparity, a right-eye display image $IM_{R2}$ illustrated in a right part of FIG. 6 is generated. In the right-eye display image $IM_{R2}$, a defective region in which pixel information is defective due to the shift is generated between the first subject B1 and the second subject B2. Such pixel information of the defective region can be interpolated on the basis of, for example, adjacent pixels. However, the interpolated pixel information may be an artifact that does not accurately reflect a situation of a real visual field. For example, another subject may exist in a gap between the first subject B1 and the second subject B2 indicated by hatching of oblique lines in FIG. 6. However, an image of such a subject that does not appear in the captured image cannot be restored by interpolation. Even in a case where image information of this gap is artificially interpolated, such image information is merely inaccurate information. In a medical scene such as surgery or diagnosis, it is desirable to avoid display of such an inaccurate image as much as possible.

Figure 7:
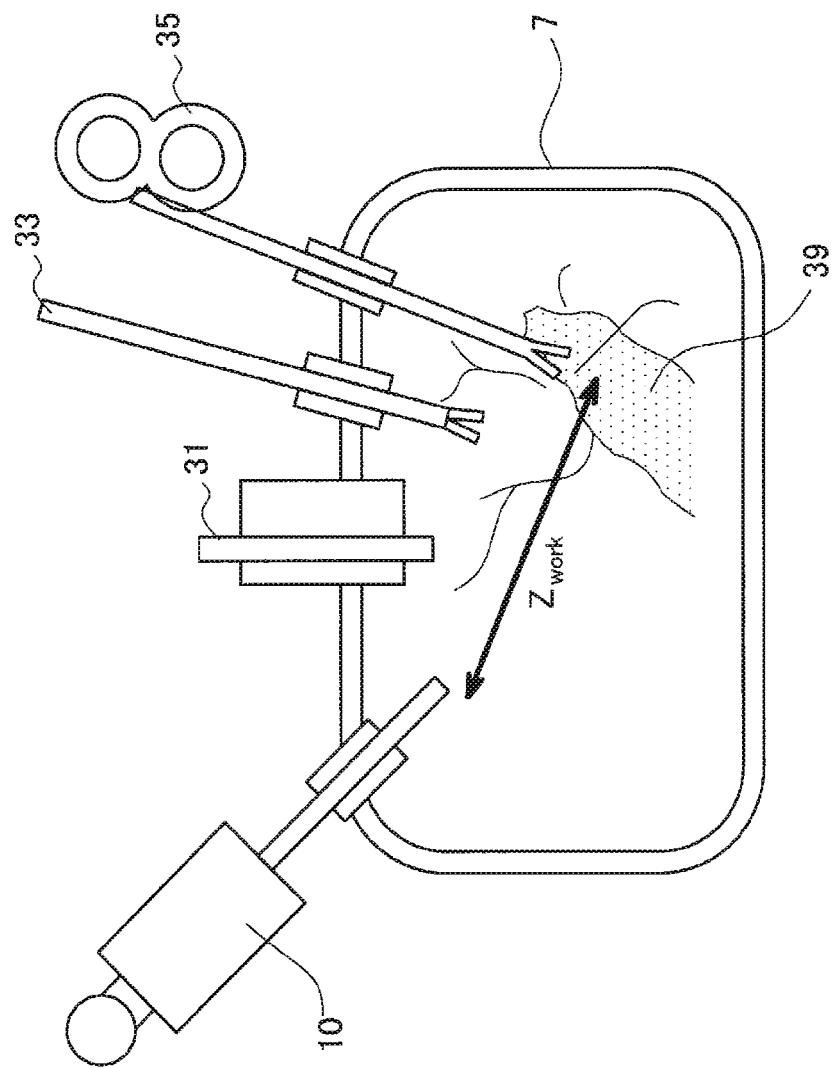
FIG. 7 is an explanatory diagram for describing an example of an operation depth of medical operation.

In view of this, embodiments described below of the technology according to the present disclosure provide mechanisms that correct a disparity with a desired correction factor within an operation depth range in which a gradation of a display depth is particularly important and reduce the correction factor out of the operation depth range. In the present specification, the operation depth means a depth at which the user (e.g., a practitioner) mainly makes close observation in medical operation. FIG. 7 is an explanatory diagram for describing an example of the operation depth of medical operation. When referring to FIG. 7, the lens barrel of the endoscope 10, the pneumoperitoneum tube 31, the energy treatment device 33, and the forceps 35 are inserted into the body cavity of the patient 7 in a scene of endoscopic surgery. An operational space is secured in the body cavity, and, for example, the forceps 35 is brought into contact with an affected part 39, and the endoscope 10 captures an image of a visual field of such operation. An operation depth $Z_{work}$ can correspond to, for example, a distance between the endoscope 10 and a tip of the forceps 35. Actually, the operation depth $Z_{work}$ may be determined by various methods, and several examples of those methods will be specifically described below. The operation depth range may be a depth range having a relatively small depth difference from such an operation depth $Z_{work}$. By sufficiently emphasizing a stereoscopic effect within the operation depth range in accordance with the technology according to the present disclosure and reducing correction of the disparity out of the operation depth range, it is possible to give a desired stereoscopic effect to the user while effectively reducing a defect of image information.

2. First Embodiment

Among the constituent elements of the medical image processing system 1 exemplified in FIG. 1, in particular, the CCU 51 functioning as an image processing device mainly relates to emphasis of a stereoscopic effect obtained by correction of a disparity. In view of this, in this section, a specific configuration of the CCU 51 according to an embodiment will be described in detail.

[2-1. Configuration Example of Image Processing Device]

Figure 8:
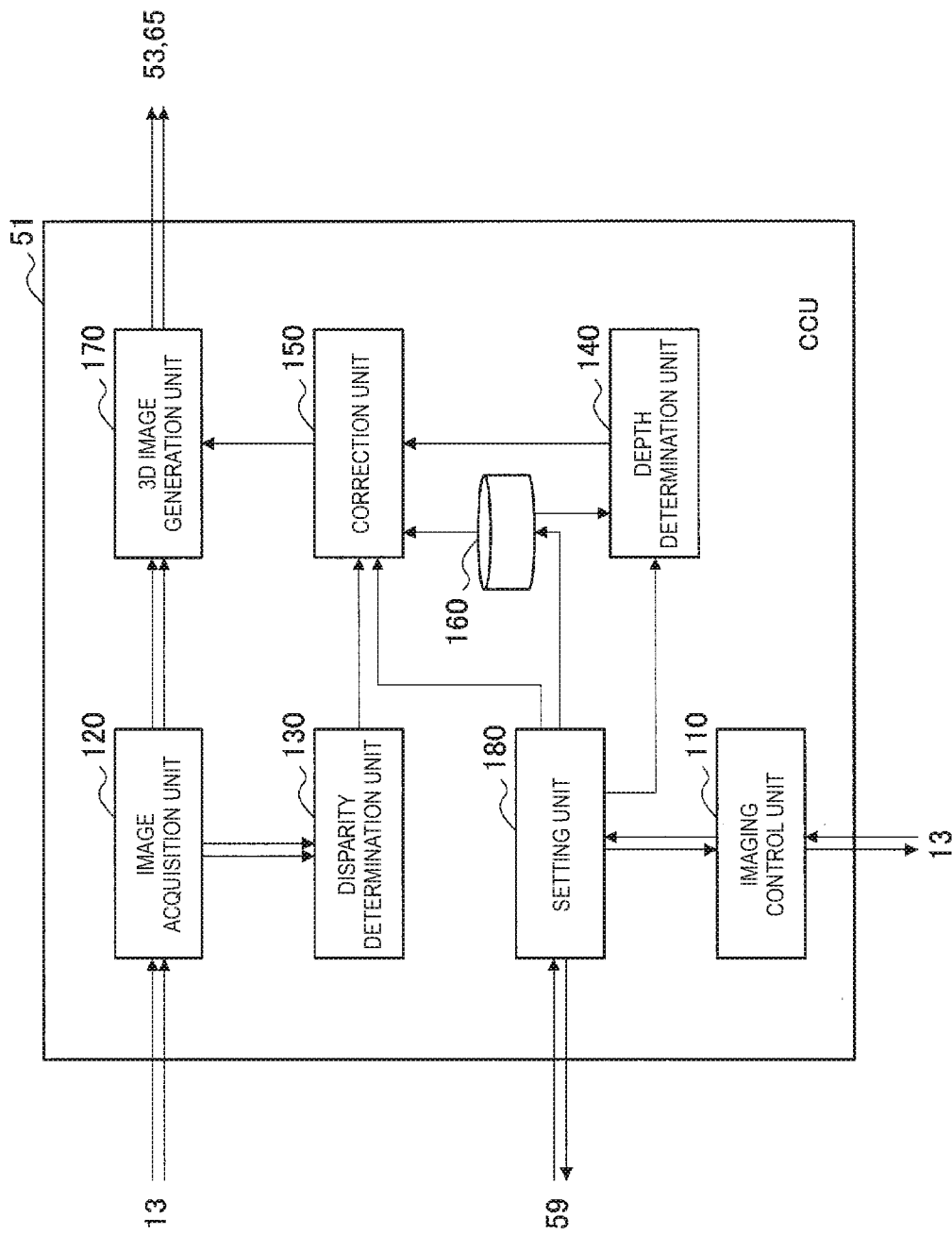
FIG. 8 is a block diagram showing an example of a configuration of an image processing device according to a first embodiment.

FIG. 8 is a block diagram illustrating an example of the configuration of the CCU 51 serving as an image processing device according to a first embodiment.

When referring to FIG. 8, the CCU 51 includes an imaging control unit 110, an image acquisition unit 120, a disparity determination unit 130, a depth determination unit 140, a correction unit 150, a storage unit 160, a 3D image generation unit 170, and a setting unit 180.

(1) Imaging Control Unit

The imaging control unit 110 controls operation of the endoscope 10 on the basis of user input and setting information detected by the input device 59 so that an image is captured as the user desires. For example, when capturing of the image is started, the imaging control unit 110 can determine an optimal focal distance by an arbitrary autofocus method such as a phase difference method or a contrast method and transmit a control signal that specifies the determined focal distance to the camera head 13. Further, the imaging control unit 110 can transmit a control signal that specifies a magnification indicated by the user to the camera head 13.

(2) Image Acquisition Unit

The image acquisition unit 120 acquires a captured image generated by a stereoscopic-vision image sensor included in the camera head 13. The captured image is an image showing an operation visual field observed in medical operation. The captured image typically includes a right-eye image and a left-eye image. The right-eye image and the left-eye image can be generated by the image sensor(s) described with reference to FIG. 2A and FIG. 2B. The image acquisition unit 120 outputs the acquired captured image to the disparity determination unit 130 and the 3D image generation unit 170.

(3) Disparity Determination Unit

The disparity determination unit 130 determines a disparity by using the captured image input from the image acquisition unit 120 and generates disparity information. The disparity determination unit 130 can search for a corresponding point in the left-eye image for each pixel position (or each pixel block) of the right-eye image in accordance with, for example, a stereo matching method and calculate a difference in horizontal position from the found corresponding point as a disparity. The disparity information generated by the disparity determination unit 130 may be, for example, disposition (e.g., a disparity map) showing the determined disparity for each pixel position (or each pixel block position). The disparity determination unit 130 outputs the disparity information that can be generated as described above to the correction unit 150.

(4) Depth Determination Unit

The depth determination unit 140 determines an operation depth of medical operation whose image is to be captured and outputs the determined operation depth to the correction unit 150. As an example, the depth determination unit 140 may determine the operation depth on the basis of the type of operation to be performed in the medical image processing system 1. Taking surgery as an example, the type of operation may be distinguished on the basis of, for example, a surgery part such as laparoscopic surgery or thoracoscopic surgery. As an unlimited example, in abdominal surgery, operation is performed at a depth of, in particular, 50 mm within a typical range of 15 to 100 mm in many cases. Meanwhile, in otolaryngologic surgery, a typical range is 2 to 50 mm and a main operation depth is reduced accordingly. Further, the type of operation may be distinguished on the basis of, for example, a surgical form such as heart bypass surgery, gastrectomy, cholecystectomy, or appendectomy. The type of operation can be set by the setting unit 180 on the basis of, for example, user input before the operation is started. Based on the setting information that associates the set type of operation with a corresponding operation depth, the depth determination unit 140 can determine an operation depth to be considered when the disparity is corrected. The depth determination unit 140 may adjust the operation depth corresponding to the type of operation (a predetermined operation depth that can be indicated by the setting information) on the basis of user input.

As another example, the depth determination unit 140 may determine the operation depth on the basis of the type of instrument to be used in the operation. As an unlimited example, a typical operation depth at which a scope having a diameter of 10 mm is used is 50 mm, and a typical operation depth at which a scope having a diameter of 4 mm is used as in otolaryngologic surgery is smaller. The type of instrument may be such a type of scope (endoscope or lens barrel thereof). Instead of this, the type of instrument may means other various types of instruments. For example, an expected operation depth in ligation in which a forceps, a needle, and a thread are used may be different from an expected operation depth in excision of a polyp in which an energy treatment device such as an electric scalpel is used. The type of instrument to be used may be set, for example, by the setting unit 180 on the basis of user input or may be automatically determined. Based on setting information that associates the type of instrument to be used with a corresponding operation depth, the depth determination unit 140 can determine an operation depth to be considered when the disparity is corrected. The depth determination unit 140 may adjust the operation depth corresponding to the type of instrument (a predetermined operation depth that can be indicated by the setting information) on the basis of user input.

As another example, the depth determination unit 140 may acquire user input that directly specifies an operation depth via, for example, the user interface and determine an operation depth to be applied when the disparity is corrected on the basis of the acquired user input. The user input herein may be any type of input such as physical input, touch input, gesture input, or audio input described regarding the input device 59.

(5) Correction Unit

The correction unit 150 corrects the disparity information input from the disparity determination unit 130 depending on the operation depth determined by the depth determination unit 140 so as to emphasize a stereoscopic effect expressed by a stereoscopic image generated on the basis of the captured image.

Figure 9:
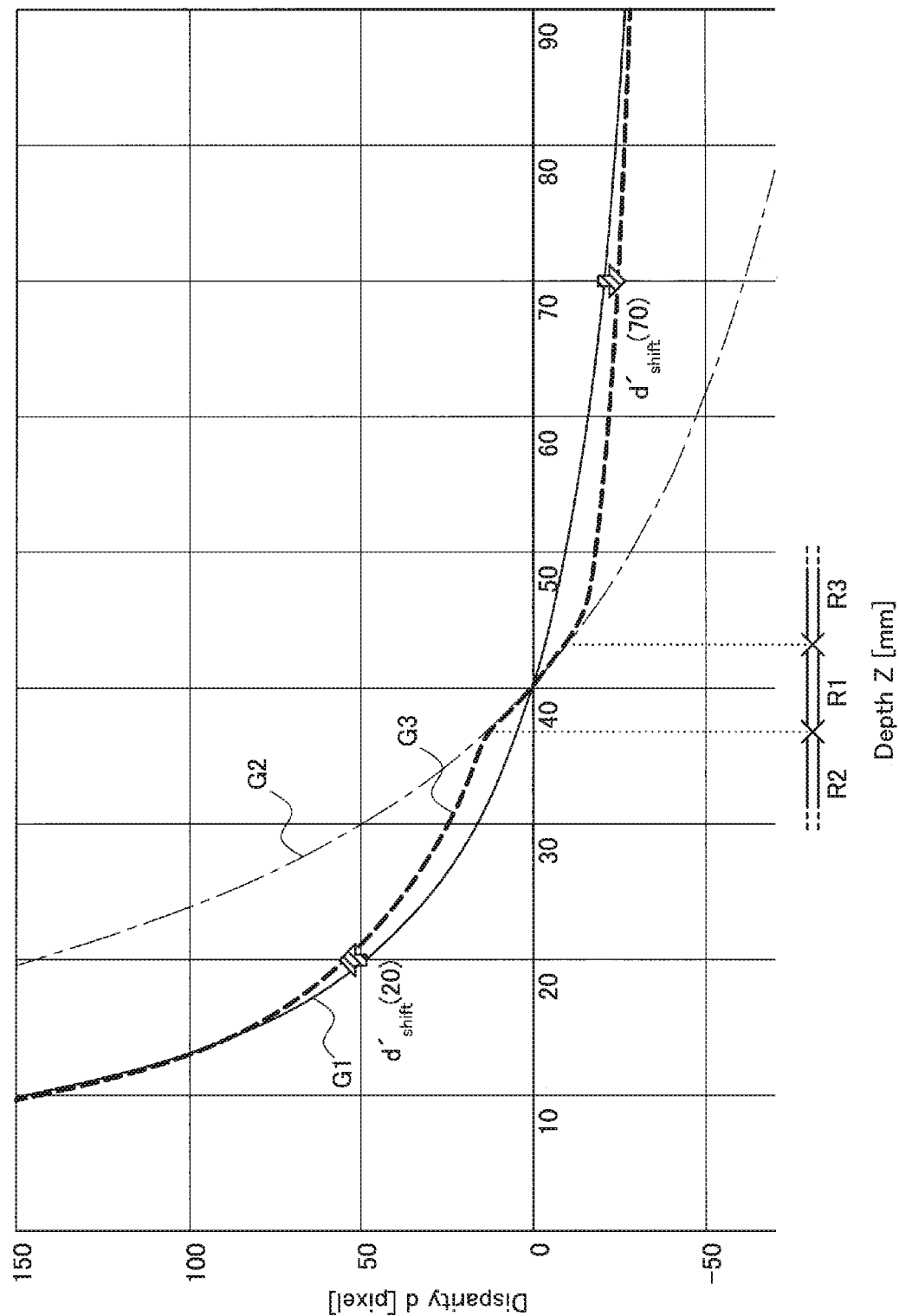
FIG. 9 is an explanatory diagram for describing an example where a correction factor for emphasizing a stereoscopic effect is reduced depending on an operation depth.

In a certain example, the correction unit 150 first determines an initial graph showing a relationship between a depth and a disparity based on an actual base length of a camera used when the image is captured. FIG. 9 shows the same graph G1 as the graph shown in FIG. 5 as the initial graph. The initial graph G1 can be determined on the basis of characteristics of the camera such as an actual base length and a focal distance. A reference depth of the initial graph G1 may be equal to the operation depth determined by the depth determination unit 140 or may be different from the operation depth. Further, the correction unit 150 determines a basic correction factor. The basic correction factor may be, for example, a ratio of the actual base length to a simulative base length. Then, the correction unit 150 derives an intermediate graph G2 that can be formed by uniformly applying the basic correction factor over the whole depth range of the initial graph G1. FIG. 9 shows the same graph G2 as the graph shown in FIG. 5 as the intermediate graph. Then, the correction unit 150 generates a correction graph G3 on the basis of the initial graph G1 and the intermediate graph G2. As an example, the correction graph G3 has a track that matches with the intermediate graph G2 within an operation depth range R1 having a small depth difference from the operation depth and is separated from the intermediate graph G2 and approaches the initial graph G1 as the depth difference from the operation depth is increased. According to correction of the disparity using such a correction graph G3, the basic correction factor (determined in accordance with the actual base length) is applied within the operation depth range R1, whereas a correction factor that is relatively reduced from the basic correction factor is applied within depth ranges R2 and R3 out of the operation depth range R1. For example, an absolute value of a shift amount necessary for correcting the disparity on the basis of the correction graph G3 is remarkably reduced at the depth Z=20 mm as indicated by an arrow shaded in FIG. 9 ($|d_{shift}(20)| > |d'_{shift}(20)|$), as compared to the case of correction based on the intermediate graph G2 (see FIG. 5). The same applies to a case of the depth Z=70 mm.

Note that the correction graph G3 shown in FIG. 9 is merely an example, and a correction graph having another track may be used. As an example, two or more operation depth ranges may be set in a single correction graph. As another example, instead of causing the correction graph to match with the intermediate graph within the operation depth range having a small depth difference from the operation depth, the correction unit 150 may generate a correction graph so that stereoscopic effect sensitivity (e.g., an inclination of the disparity from the depth) does not fall below a required lower limit within the operation depth range. By setting the lower limit of the stereoscopic effect sensitivity within the operation depth range as described above, it is possible to prevent emphasis of the stereoscopic effect obtained as a result of reducing the correction factor of the disparity from being insufficient. Such a lower limit is not set out of the operation depth range.

As another example, the correction unit 150 may generate a correction graph in which the correction factor within a depth range out of the operation depth range is reduced so that an index regarding a defect amount of pixel information caused by correction of the disparity does not exceed an upper limit. The index regarding the defect amount of pixel information may be, for example, a proportion of the number of pixels in a defective region to the number of pixels of the whole or part of the image, a maximum width of the defective region, or the like. By imposing a restriction of the index regarding the defect amount of pixel information on the correction graph as described above, at least a certain level of accuracy is secured in an image after the stereoscopic effect is corrected.

In a certain example, the correction unit 150 may dynamically generate a correction graph. The characteristics of the camera (e.g., an actual base length and a focal distance) necessary for generating a correction graph can be provided by the imaging control unit 110 or the setting unit 180. Parameters necessary for determining a correction graph, such as a pseudo base length or a basic correction factor, a width of the operation depth range, the lower limit of the stereoscopic effect sensitivity of the operation depth range, and the upper limit of the index regarding the defect amount of pixel information, may be defined in advance or may be specified by user input.

In another example, the correction unit 150 may acquire a correction graph set in advance and stored on the storage unit 160. The correction unit 150 may select, for example, one of a plurality of possible graphs corresponding to a plurality of combinations of the operation depth, the characteristics of the camera, and other variable parameters (e.g., a pseudo base length or a basic correction factor) on the basis of user input. Further, as described below, a correction graph showing a relationship between a depth and a corrected disparity may be set in advance by the user via, for example, a graphical user interface (GUI).

Note that, in any example, a table showing a difference between the correction graph and the initial graph (i.e., a shift amount) at each depth may be set or generated in addition to or instead of the correction graph. In the following description, data in such a table format will be referred to as "correction profile".

The correction unit 150 corrects the disparity information input from the disparity determination unit 130 in accordance with the correction graph (or the correction profile) that can be derived by any one of the methods described above. For example, based on the disparity for each pixel position indicated by the disparity information, the correction unit 150 first determines the depth of the subject appearing at the pixel position. Then, the correction unit 150 adds the shift amount corresponding to the difference between the correction graph and the initial graph, the shift amount corresponding to the determined depth of the subject, to the disparity at the pixel position (or subtracts the shift amount from the disparity). As a result of repetition of such calculation for each pixel position (or each pixel block), corrected disparity information can be generated. The correction unit 150 outputs the corrected disparity information to the 3D image generation unit 170.

(6) Storage Unit

The storage unit 160 can store various pieces of setting information. The setting information may include, for example, operation information that associates each of a plurality of types of possible operation with a corresponding operation depth. Further, the setting information may include instrument information that associates each of types of possible instruments to be used in operation with a corresponding operation depth. Further, the setting information may include operation depth information that directly specifies the operation depth.

Further, the storage unit 160 can store parameters for deriving an initial graph and a correction graph. For example, the storage unit 160 may store camera characteristic parameters such as an actual base length and a focal distance in the camera head 13. Further, the storage unit 160 may store graph-related parameters that can include one or more of the pseudo base length, the basic correction factor, the width of the operation depth range, the lower limit of the stereoscopic effect sensitivity in the operation depth range, and the upper limit of the index regarding the defect amount of pixel information. Further, the storage unit 160 may store an initial graph and a correction graph (or a correction profile).

(7) 3D image Generation Unit

The 3D image generation unit 170 generates a stereoscopic image corresponding to a visual field observed in medical operation by using the corrected disparity information input from the correction unit 150. For example, the 3D image generation unit 170 shifts a horizontal position of a pixel in at least one of the right-eye image and left-eye image input from the image acquisition unit 120 in accordance with the disparity indicated by the corrected disparity information, thereby generating a stereoscopic image. In a defective region in which pixel information is defective because the horizontal position of the pixel is shifted, the 3D image generation unit 170 may interpolate pixel information on the basis of adjacent pixels having no defect. In the present embodiment, only a small defective region is generated due to reduction in the correction factor of the disparity, and therefore a proportion of an artifact caused by interpolation of the pixel information is smaller than the proportion thereof in existing technologies. The stereoscopic image includes the right-eye display image and the left-eye display image. The 3D image generation unit 170 outputs a display image signal showing the generated stereoscopic image to the display device 53 (and/or the recorder 65).

(8) Setting Unit

The setting unit 180 manages various settings for generating and displaying a stereoscopic image in the medical image processing system 1 in accordance with user input detected via the input device 59 and an imaging condition controlled by the imaging control unit 110. The setting unit 180 may accept user input that specifies the type of operation from the user (e.g., a practitioner) before, for example, the use of the medical image processing system 1 is started. Further, the setting unit 180 may accept user input that specifies the type of instrument to be used in operation or may automatically determine the type of instrument. Further, the setting unit 180 may accept user input that specifies an operation depth at which the user mainly makes close observation in operation. For example, the setting unit 180 may provide the user interface that presents those plurality of possible settings (e.g., display the plurality of possible settings on the display device 53 or another screen) and cause the user to select one of the possible settings.

Further, the setting unit 180 may accept user input that specifies or selects the graph-related parameters that can be used to derive an initial graph and a correction graph. For example, the user interface for causing the user to set a restricting condition such as the lower limit of the stereoscopic effect sensitivity within the operation depth range or the upper limit of the index regarding the defect amount of pixel information is provided, and therefore the user can flexibly adjust display of stereoscopic vision in accordance with a purpose (e.g., desired sensitivity, an allowable proportion of an artifact, or the like). Further, the setting unit 180 may provide, for example, a graphical user interface (GUI) for causing the user to edit a correction graph to be applied when a stereoscopic image is generated (e.g., a GUI that allows a track of a displayed graph to be moved by touching or dragging).

[2-2. Flow of Processing]

In this section, examples of a flow of processing that can be executed by the CCU 51 in the above embodiment will be described with reference to several flowcharts. Note that, although a plurality of processing steps are shown in the flowcharts, those processing steps do not necessarily need to be executed in order shown in the flowcharts. Several processing steps may be executed in parallel. Further, an additional processing step may be employed, or part of the processing steps may be omitted. The same applies to description of embodiments in the following sections.

(1) Stereoscopic Image Generation Processing

Figure 10:
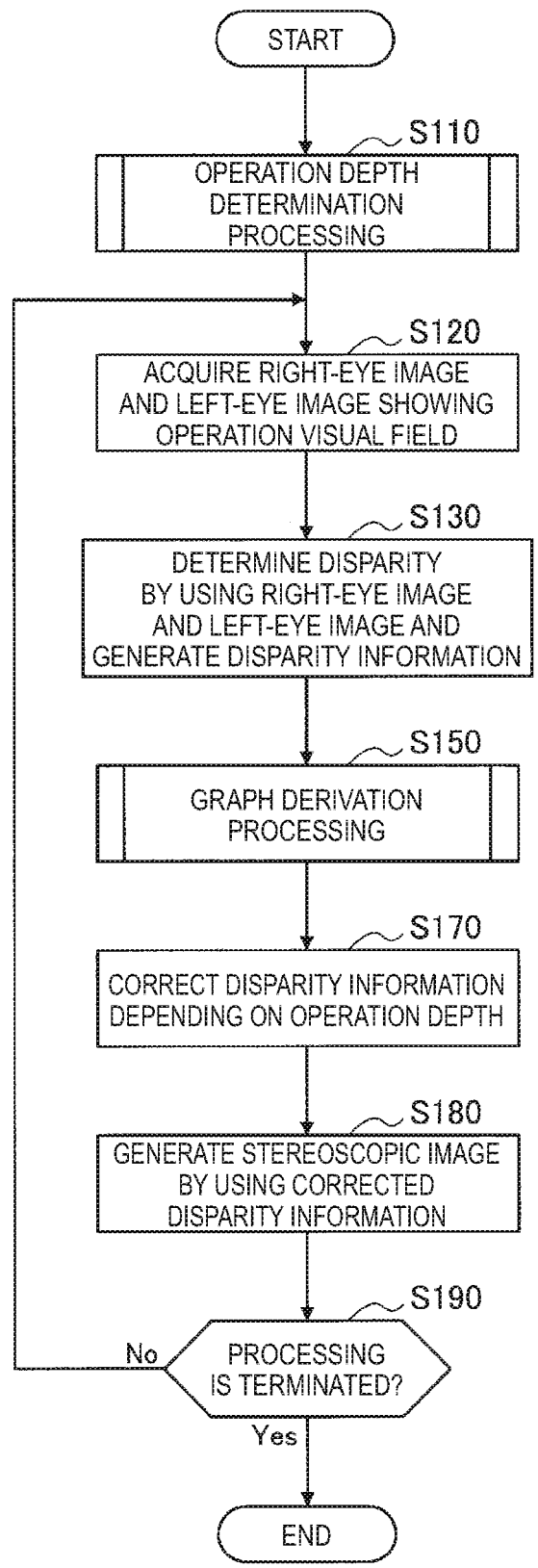
FIG. 10 is a flowchart showing an example of a flow of stereoscopic image generation processing according to the first embodiment.

FIG. 10 is a flowchart showing an example of a flow of stereoscopic image generation processing that can be executed by the CCU 51 according to the first embodiment. When referring to FIG. 10, first, the depth determination unit 140 executes operation depth determination processing in order to determine an operation depth of medical operation whose image is to be captured before capturing of an image is started (Step S110). Several examples of a more detailed flow of the operation depth determination processing executed herein will be further described below.

Then, the image acquisition unit 120 acquires a right-eye image and left-eye image that are generated by the stereoscopic-vision image sensor and show an operation visual field (Step S120). Then, the disparity determination unit 130 determines a disparity for each pixel position by using the right-eye image and left-eye image acquired by the image acquisition unit 120 and generates disparity information (Step S130). The disparity determination unit 130 outputs the disparity information that can be generated as described above to the correction unit 150.

Then, the correction unit 150 executes graph derivation processing in order to determine how to correct the disparity information generated by the disparity determination unit 130 depending on the operation depth (Step S150). Several examples of a more detailed flow of the graph derivation processing executed herein will be further described below.

Then, the correction unit 150 executes correction of the disparity information depending on the operation depth by using a correction graph (or a correction profile showing a difference between the correction graph and an initial graph) derived as a result of the graph derivation processing (Step S170).

Then, the 3D image generation unit 170 shifts a horizontal position of each pixel of a subject in at least one of the right-eye image and left-eye image acquired by the image acquisition unit 120 by using the disparity information corrected by the correction unit 150, thereby generating a stereoscopic image (Step S180). A display image signal showing the stereoscopic image generated by the 3D image generation unit 170 may be output to, for example, the display device 53 in order to display the stereoscopic image or may be output to the recorder 65 in order to record the image or a moving image.

Steps S120 to S180 described above are repeated until a termination condition of the stereoscopic image generation processing is satisfied (Step S190). For example, when user input to give an instruction to terminate the processing is detected via the input device 59, the above stereoscopic image generation processing is terminated. Note that the operation depth determination processing in Step S110 may be executed again while the stereoscopic image generation processing is being continued and the operation depth may be updated.

(2) Operation Depth Determination Processing

Figure 11A:
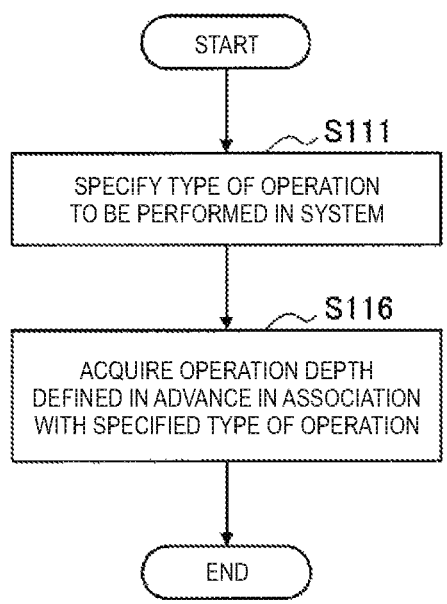
FIG. 11A is a flowchart showing a first example of a detailed flow of operation depth determination processing shown in FIG. 10.

FIG. 11A is a flowchart showing a first example of the detailed flow of the operation depth determination processing shown in FIG. 10. When referring to FIG. 11A, first, the depth determination unit 140 specifies the type of operation to be performed in the medical image processing system 1 (Step S111). For example, the type of operation can be indicated by setting information stored in advance on the storage unit 160 or can be specified by user input. Then, the depth determination unit 140 acquires an operation depth defined in advance in association with the specified type of operation from the setting information (Step S116).

Figure 11B:
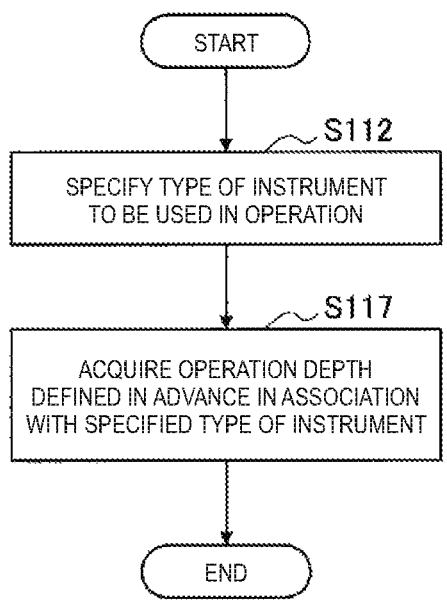
FIG. 11B is a flowchart showing a second example of a detailed flow of operation depth determination processing shown in FIG. 10.

FIG. 11B is a flowchart showing a second example of the detailed flow of the operation depth determination processing shown in FIG. 10. When referring to FIG. 11B, first, the depth determination unit 140 specifies the type of instrument to be used in operation to be performed in the medical image processing system 1 (Step S112). Then, the depth determination unit 140 acquires an operation depth defined in advance in association with the determined type of instrument from the setting information (Step S117).

Figure 11C:
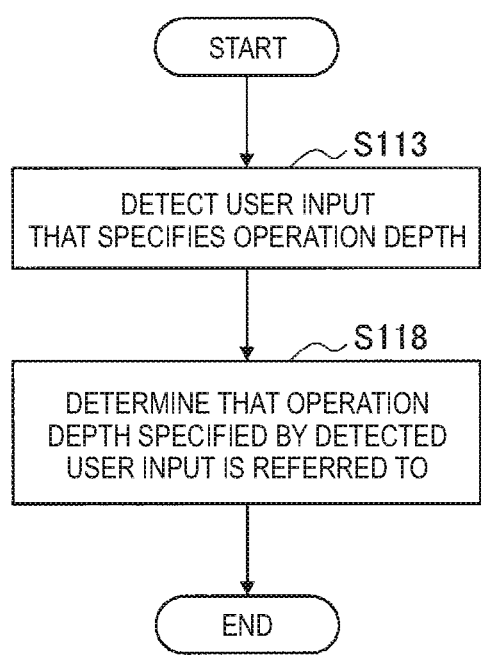
FIG. 11C is a flowchart showing a third example of a detailed flow of operation depth determination processing shown in FIG. 10.

FIG. 11C is a flowchart showing a third example of the detailed flow of the operation depth determination processing shown in FIG. 10. When referring to FIG. 11C, the depth determination unit 140 detects user input that directly specifies an operation depth via, for example, the user interface provided by the setting unit 180 (Step S113). Then, the depth determination unit 140 determines that the operation depth specified by the detected user input is referred to when a stereoscopic image is generated (Step S118).

(3) Graph Derivation Processing

Figure 12A:
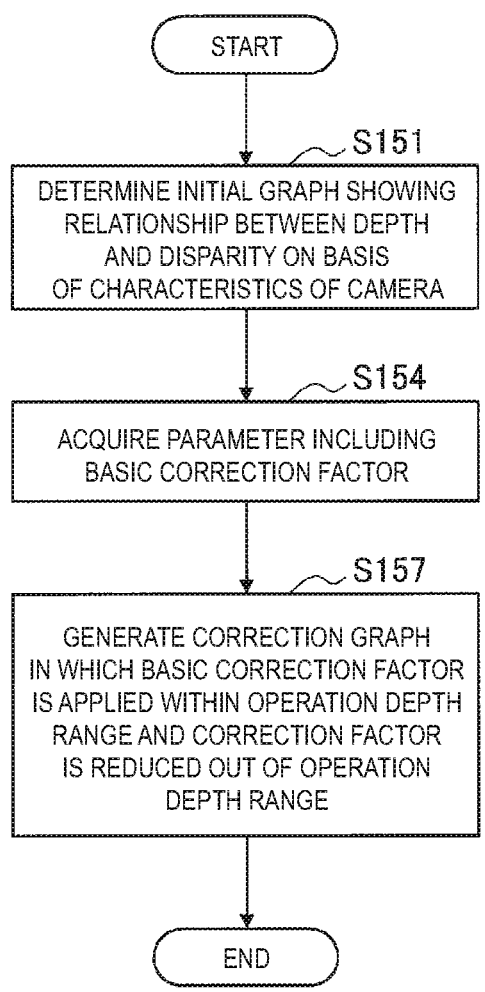
FIG. 12A is a flowchart showing a first example of a detailed flow of graph derivation processing shown in FIG. 10.

FIG. 12A is a flowchart showing a first example of the detailed flow of the graph derivation processing shown in FIG. 10. When referring to FIG. 12A, first, the correction unit 150 determines an initial graph showing a relationship between an uncorrected depth and a disparity on the basis of the characteristics of the camera such as an actual base length and a focal distance (Step S151). Further, the correction unit 150 acquires a parameter including, for example, a basic correction factor that is a ratio of an actual base length to a simulative base length (Step S154). Then, the correction unit 150 generates a correction graph in which the basic correction factor is applied within an operation depth range having a small depth difference from the operation depth determined by the depth determination unit 140 and the correction factor is reduced out of the operation depth range (Step S157).

Figure 12B:
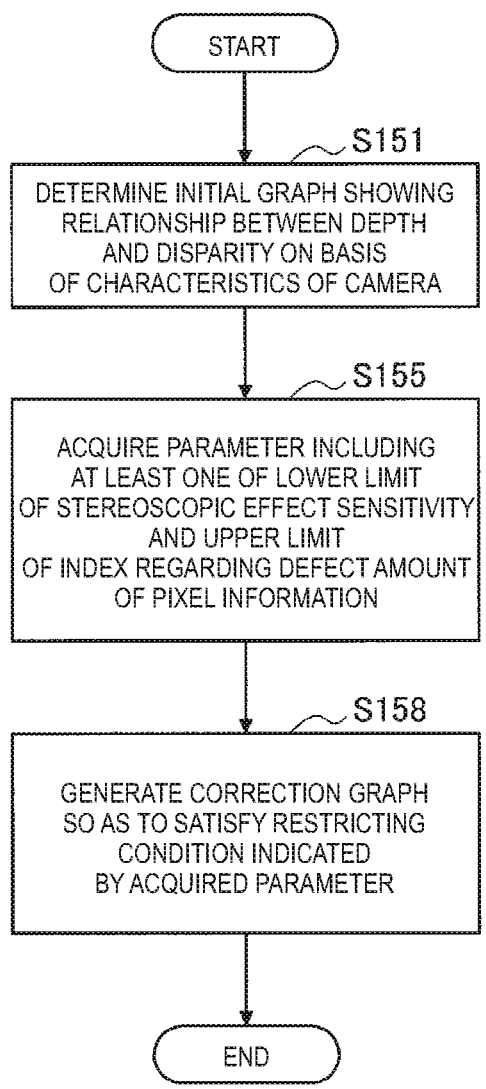
FIG. 12B is a flowchart showing a second example of a detailed flow of graph derivation processing shown in FIG. 10.

FIG. 12B is a flowchart showing a second example of the detailed flow of the graph derivation processing shown in FIG. 10. When referring to FIG. 12B, first, the correction unit 150 determines an initial graph showing a relationship between an uncorrected depth and a disparity on the basis of the characteristics of the camera such as an actual base length and a focal distance (Step S151). Further, the correction unit 150 acquires a parameter including at least one of the lower limit of the stereoscopic effect sensitivity and the upper limit of the index regarding the defect amount of pixel information (Step S155). Then, the correction unit 150 generates a correction graph that satisfies a restricting condition indicated by the acquired parameter (Step S158). The correction graph generated herein can have, for example, stereoscopic effect sensitivity (e.g., an inclination of the disparity from the depth) that does not fall below the lower limit indicated by the parameter within an operation depth range having a small depth difference from the operation depth. Further, the index regarding the defect amount of pixel information over the whole depth range of the correction graph does not exceed the upper limit indicated by the parameter.

Figure 12C:
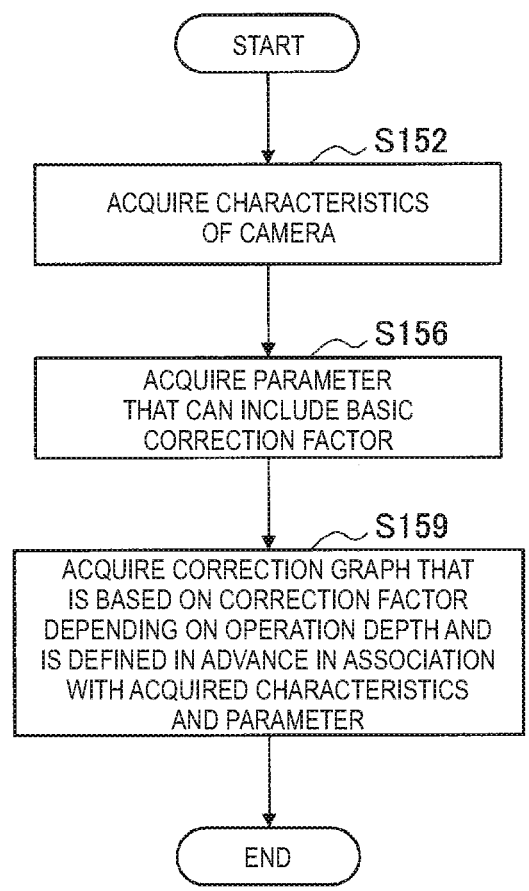
FIG. 12C is a flowchart showing a third example of a detailed flow of graph derivation processing shown in FIG. 10.

FIG. 12C is a flowchart showing a third example of the detailed flow of the graph derivation processing shown in FIG. 10. When referring to FIG. 12A, first, the correction unit 150 acquires the characteristics of the camera such as an actual base length and a focal distance (Step S152). Further, the correction unit 150 acquires, for example, a parameter that can include a basic correction factor (Step S156). Then, the correction unit 150 acquires a correction graph that is based on a correction factor depending on the operation depth and is defined in advance in association with the acquired characteristics and parameter from the storage unit 160 (Step S159).

3. Second Embodiment

In the first embodiment, an operation depth of medical operation is determined on the basis of user input or setting information before capturing of an image is started. Meanwhile, in a second embodiment that will be described in this section, an operation depth of medical operation is determined on the basis of analysis of a captured image.

[3-1. Configuration Example of Image Processing Device]

Figure 13:
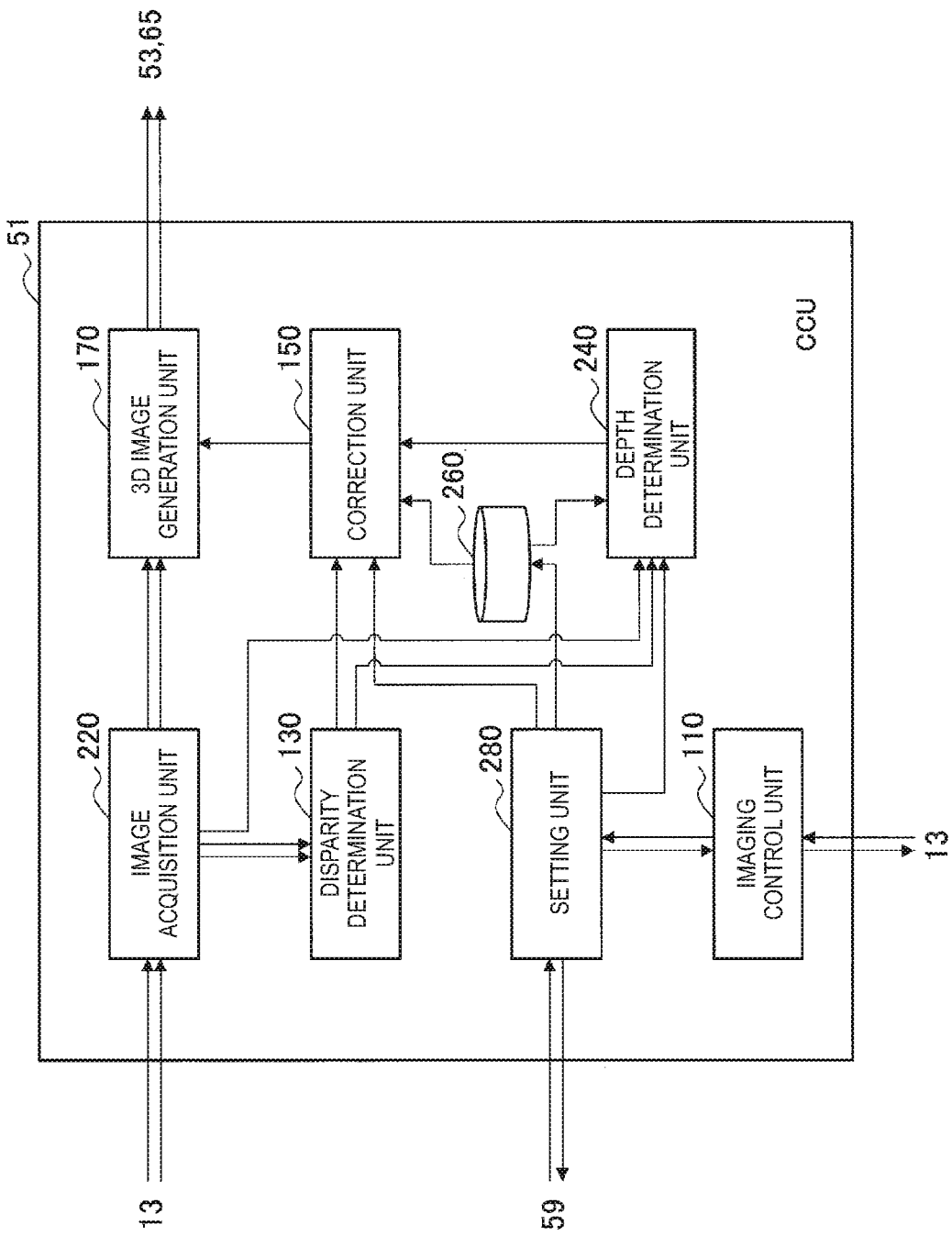
FIG. 13 is a block diagram illustrating an example of a configuration of an image processing device according to a second embodiment.

FIG. 13 is a block diagram illustrating an example of a configuration of the CCU 51 serving as an image processing device according to the second embodiment. When referring to FIG. 13, the CCU 51 includes the imaging control unit 110, an image acquisition unit 220, the disparity determination unit 130, a depth determination unit 240, the correction unit 150, a storage unit 260, the 3D image generation unit 170, and a setting unit 280.

The image acquisition unit 220 acquires a captured image generated by the stereoscopic-vision image sensor included in the camera head 13. The captured image is an image showing an operation visual field observed in medical operation and typically includes a right-eye image and a left-eye image. The image acquisition unit 220 outputs the acquired captured image to the disparity determination unit 130, the depth determination unit 240, and the 3D image generation unit 170.

The depth determination unit 240 determines an operation depth of medical operation whose image is to be captured and outputs the determined operation depth to the correction unit 150. As a first example, the depth determination unit 240 determines the operation depth on the basis of a depth determined regarding an instrument recognized in the captured image. Specifically, the depth determination unit 240 acquires an already-known image feature value of a target instrument to be recognized, which is set by the setting unit 280, from the storage unit 260. Then, the depth determination unit 240 collates an image feature value extracted for each block of the captured image (e.g., one of the right-eye image and the left-eye image) with the above already-known image feature value of the target instrument, thereby determining which position in the captured image the target instrument appears. Further, the depth determination unit 240 determines a depth at which the target instrument exists on the basis of a disparity determined by the disparity determination unit 130 at the position at which the target instrument appears. The depth determination unit 240 may determine that the depth determined as described above is an operation depth at which the user mainly makes close observation in operation. Note that a plurality of target instruments may be set as the instrument to be recognized. In a case where a plurality of target instruments are detected in the captured image, the depth determination unit 240 may calculate a representative value such as an average value, a median value, or a minimum value on the basis of depths of those target instruments and determine the representative value as the operation depth.

As a second example, the depth determination unit 240 recognizes a subject that is in focus in the captured image and determines an operation depth on the basis of a depth determined regarding the recognized subject. Specifically, the depth determination unit 240 evaluates a contrast index for each block of the captured image (e.g., one of the right-eye image and the left-eye image) and determines that a subject existing at a position of a block indicating the highest index value is in focus. Then, the depth determination unit 240 determines a depth at which the subject in focus exists on the basis of a disparity determined by the disparity determination unit 130 at the position of the subject. The depth determination unit 240 may determine that the depth determined as described above is an operation depth at which the user mainly makes close observation in operation.

The storage unit 260 stores not only the setting information and parameters that have been described regarding the storage unit 160 according to the first embodiment but also, in the above first example, the already-known image feature value of each of the one or more instruments to be used when the operation depth is determined together with an identifier of each of the instruments.

The setting unit 280 manages not only the setting that has been described regarding the setting unit 180 according to the first embodiment but also setting of image analysis for determining the operation depth. Specifically, in the above first example, the setting unit 280 sets one or more instruments to be recognized in the captured image in order to determine the operation depth as a target instrument. The setting unit 280 may accept, for example, user input that specifies an instrument to be recognized from the user (e.g., a practitioner) before the use of the medical image processing system 1 is started. The setting unit 280 may determine instruments connected to the system and set, as a target instrument, an instrument that is selected by the user or is automatically selected according to some rule from the determined instruments.

By determining an operation depth of medical operation on the basis of analysis of a captured image in accordance with the present embodiment, even in a case where a depth of actual operation is changed over time, it is possible to cause the operation depth to follow the change. For example, at a depth of a target instrument closely observed by the user or a subject in focus and within an operation depth range in the vicinity of the depth, it is possible to continuously emphasize a stereoscopic effect, regardless of a change in the depth, and it is possible to reduce a defect of pixel information within a depth range far therefrom.

[3-2. Flow of Processing]

(1) Stereoscopic Image Generation Processing

Figure 14:
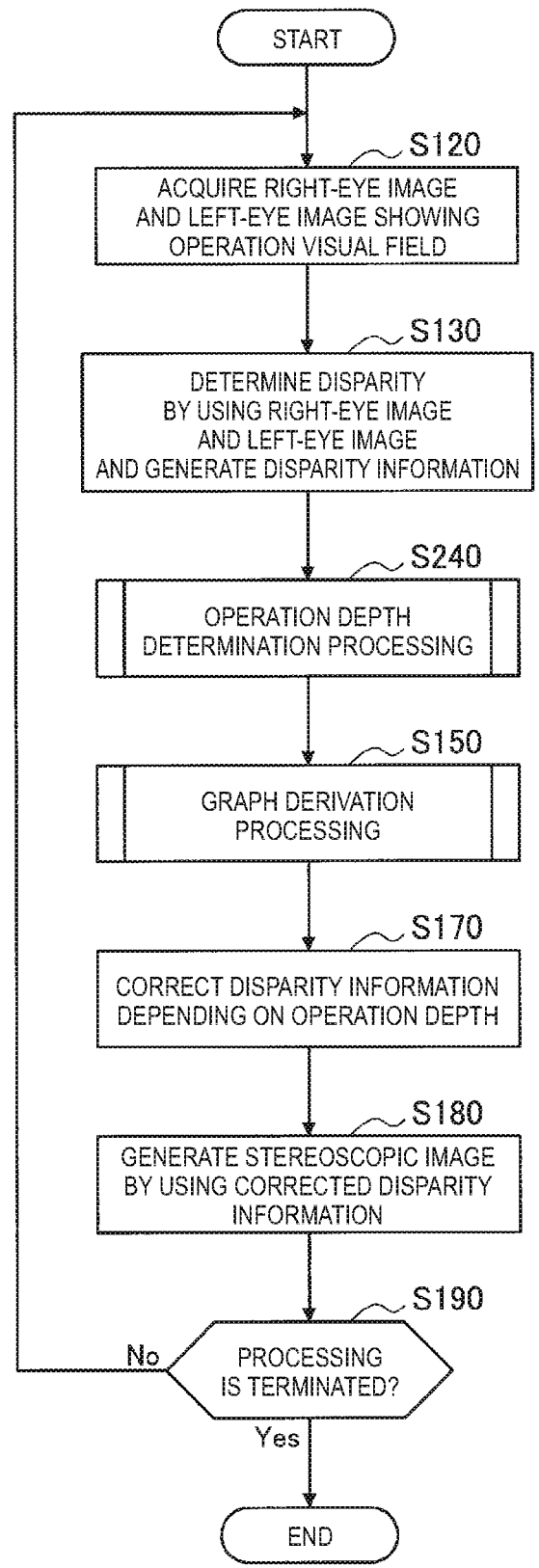
FIG. 14 is a flowchart showing an example of a flow of stereoscopic image generation processing according to the second embodiment.

FIG. 14 is a flowchart showing an example of a flow of stereoscopic image generation processing that can be executed by the CCU 51 according to the second embodiment. When referring to FIG. 14, first, the image acquisition unit 220 acquires a right-eye image and left-eye image that are generated by the stereoscopic-vision image sensor and show an operation visual field (Step S120).

Then, the disparity determination unit 130 determines a disparity for each pixel position by using the right-eye image and left-eye image acquired by the image acquisition unit 120 and generates disparity information (Step S130). The disparity determination unit 130 outputs the disparity information that can be generated as described above to the depth determination unit 240 and the correction unit 150.

Then, the depth determination unit 240 executes operation depth determination processing in order to determine an operation depth of medical operation whose image is to be captured (Step S240). Several examples of a detailed flow of the operation depth determination processing executed herein will be further described below.

Then, the correction unit 150 executes graph derivation processing in order to determine how to correct the disparity information generated by the disparity determination unit 130 depending on the operation depth (Step S150). The graph derivation processing executed herein may be similar to, for example, the processing described with reference to FIGS. 12A to 12C.

Then, the correction unit 150 executes correction of the disparity information depending on the operation depth by using a correction graph (or a correction profile showing a difference between the correction graph and an initial graph) derived as a result of the graph derivation processing (Step S170).

Then, the 3D image generation unit 170 shifts a horizontal position of each pixel of a subject in at least one of the right-eye image and left-eye image acquired by the image acquisition unit 220 by using the disparity information corrected by the correction unit 150, thereby generating a stereoscopic image (Step S180).

Steps S120 to S180 described above are repeated until a termination condition of the stereoscopic image generation processing is satisfied (Step S190). For example, when user input to give an instruction to terminate the processing is detected via the input device 59, the above stereoscopic image generation processing is terminated.

(2) Operation Depth Determination Processing

Figure 15A:
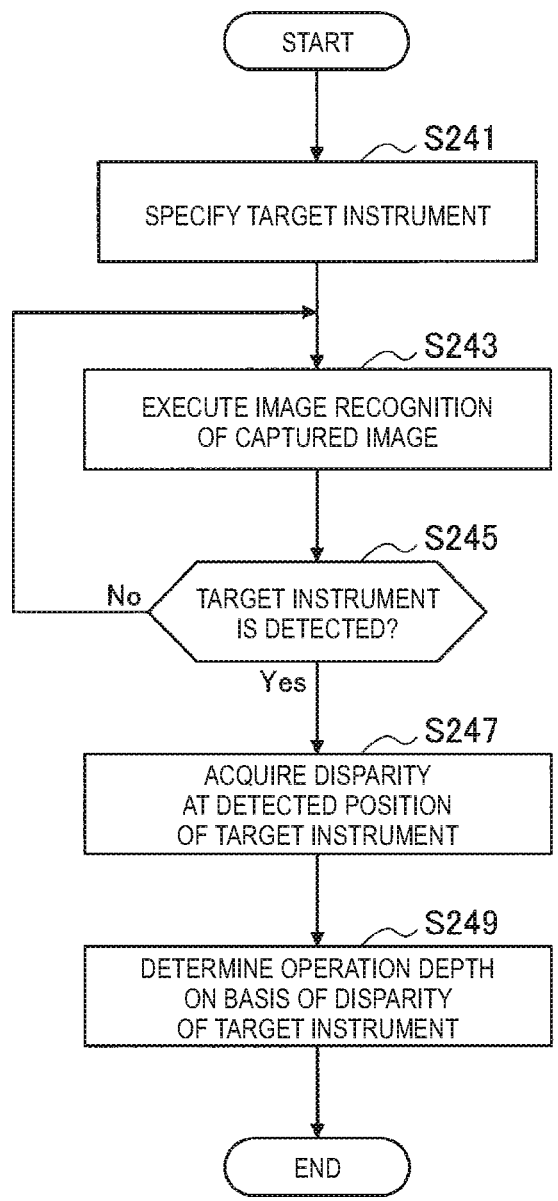
FIG. 15A is a flowchart showing a first example of a detailed flow of operation depth determination processing according to the second embodiment.

FIG. 15A is a flowchart showing a first example of the detailed flow of the operation depth determination processing shown in FIG. 14. When referring to FIG. 15A, first, the depth determination unit 240 specifies a target instrument to be recognized, which can be set in advance by the setting unit 280 (Step S241). Then, the depth determination unit 240 executes image recognition for recognizing the target instrument in the captured image (Step S243). The image recognition herein is repeated until, for example, the target instrument is detected in the captured image (Step S245). Then, when the target instrument is detected as a result of the image recognition, the depth determination unit 240 acquires a disparity indicated by the disparity information at the detected position (Step S247). Then, the depth determination unit 240 determines that a depth calculated on the basis of the acquired disparity of the target instrument is an operation depth at which the user mainly makes close observation (Step S249).

Figure 15B:
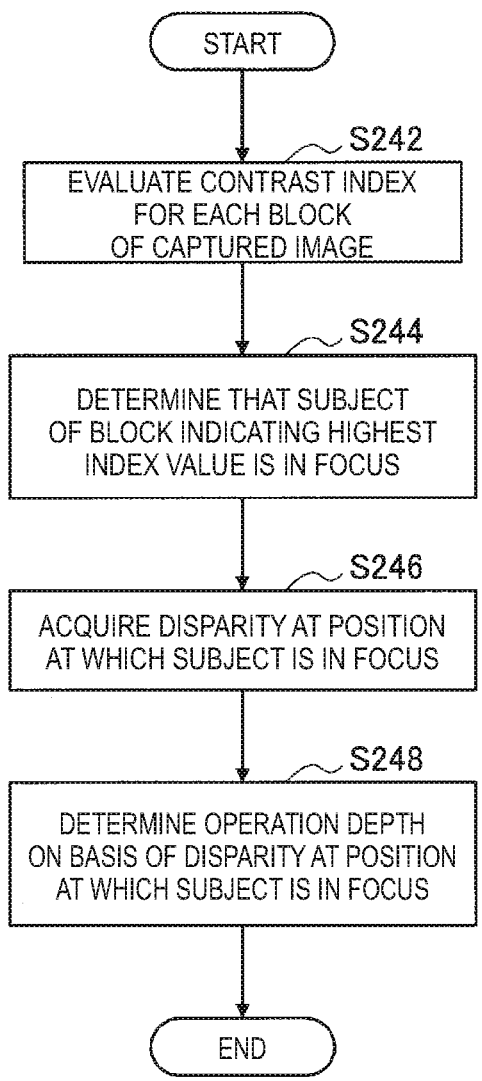
FIG. 15B is a flowchart showing a second example of a detailed flow of operation depth determination processing according to the second embodiment.

FIG. 15B is a flowchart showing a second example of the detailed flow of the operation depth determination processing shown in FIG. 14. When referring to FIG. 15B, first, the depth determination unit 240 evaluates a contrast index for each block of the captured image (Step S242). Then, the depth determination unit 240 determines that a subject existing at a position of a block indicating the highest contrast index value is in focus (Step S244). Then, the depth determination unit 240 acquires a disparity indicated by the disparity information at the position at which the subject is in focus (Step S246). Then, the depth determination unit 240 determines the disparity at the position at which the subject is in focus as an operation depth at which the user mainly makes close observation (Step S248).

4. Third Embodiment

In a third embodiment that will be described in this section, an operation depth of medical operation is determined on the basis of an imaging condition to be determined when an image of an operation visual field is captured, instead of being determined before capturing of an image is started.

[4-1. Configuration Example of Image Processing Device]

Figure 16:
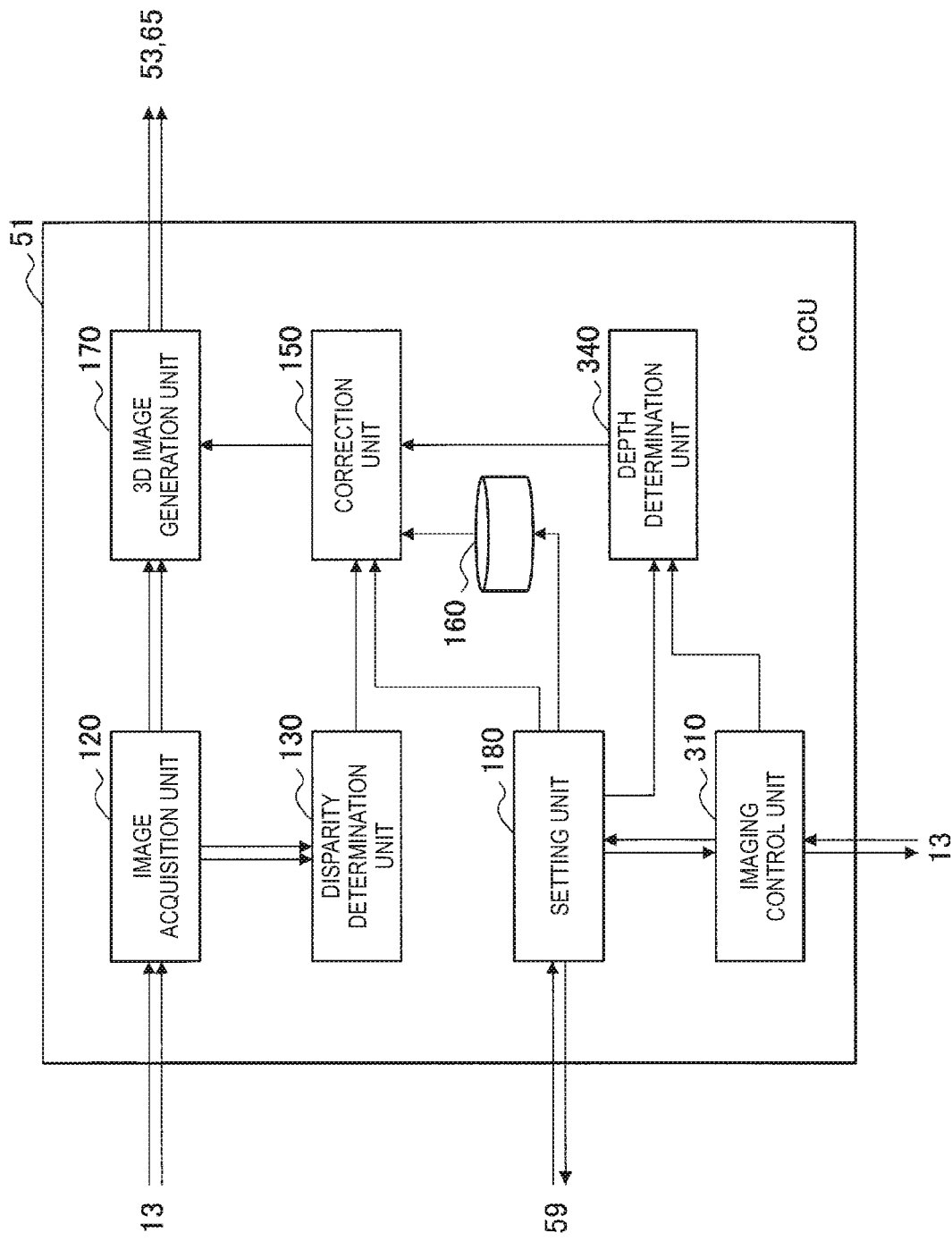
FIG. 16 is a block diagram illustrating an example of a configuration of an image processing device according to a third embodiment.

FIG. 16 is a block diagram illustrating an example of a configuration of the CCU 51 serving as an image processing device according to the third embodiment. When referring to FIG. 16, the CCU 51 includes an imaging control unit 310, the image acquisition unit 120, the disparity determination unit 130, a depth determination unit 340, the correction unit 150, the storage unit 160, the 3D image generation unit 170, and the setting unit 180.

The imaging control unit 310 controls operation of the endoscope 10 on the basis of user input and setting information detected by the input device 59 so that an image is captured as the user desires. For example, when capturing of the image is started, the imaging control unit 310 can determine an optimal focal distance on the basis of, for example, evaluation of a phase difference between a plurality of possible focus points and transmit a control signal that specifies the determined focal distance to the camera head 13. Further, in the present embodiment, the imaging control unit 310 outputs imaging condition information indicating the optimal focal distance and a selected focus point position (which is in focus) to the depth determination unit 340.

The depth determination unit 340 determines an operation depth of medical operation whose image is to be captured and outputs the determined operation depth to the correction unit 150. In the present embodiment, the depth determination unit 340 determines the operation depth on the basis of an imaging condition to be determined when an image of an operation visual field is captured. As an example, the depth determination unit 340 may roughly estimate a depth of a subject by multiplying the focal distance indicated by the imaging condition information input from the imaging control unit 310 by a coefficient. The coefficient herein may be fixedly defined in advance. Instead of this, the depth determination unit 340 may dynamically determine the coefficient depending on, for example, characteristics of a camera such as a diameter of the image sensor. As another example, the depth determination unit 340 may determine a depth at which the subject in focus exists on the basis of a disparity determined by the disparity determination unit 130 at the selected focus point position indicated by the imaging condition information. Then, the depth determination unit 340 can determine that the depth of the subject determined by any one of the methods is an operation depth at which the user mainly makes close observation.

By determining the operation depth on the basis of the imaging condition determined when the image of the operation visual field has been captured in accordance with the present embodiment, it is possible to easily track the depth of the subject that is changeable during operation as the operation depth, without executing image analysis that needs comparatively many calculation costs. In addition, it is possible to continuously emphasize a stereoscopic effect at such a depth of the subject and within an operation depth range in the vicinity of the depth and reduce a defect of pixel information within a depth range out of the operation depth range.

[4-2. Flow of Processing]
(1) Stereoscopic Image Generation Processing

Figure 17:
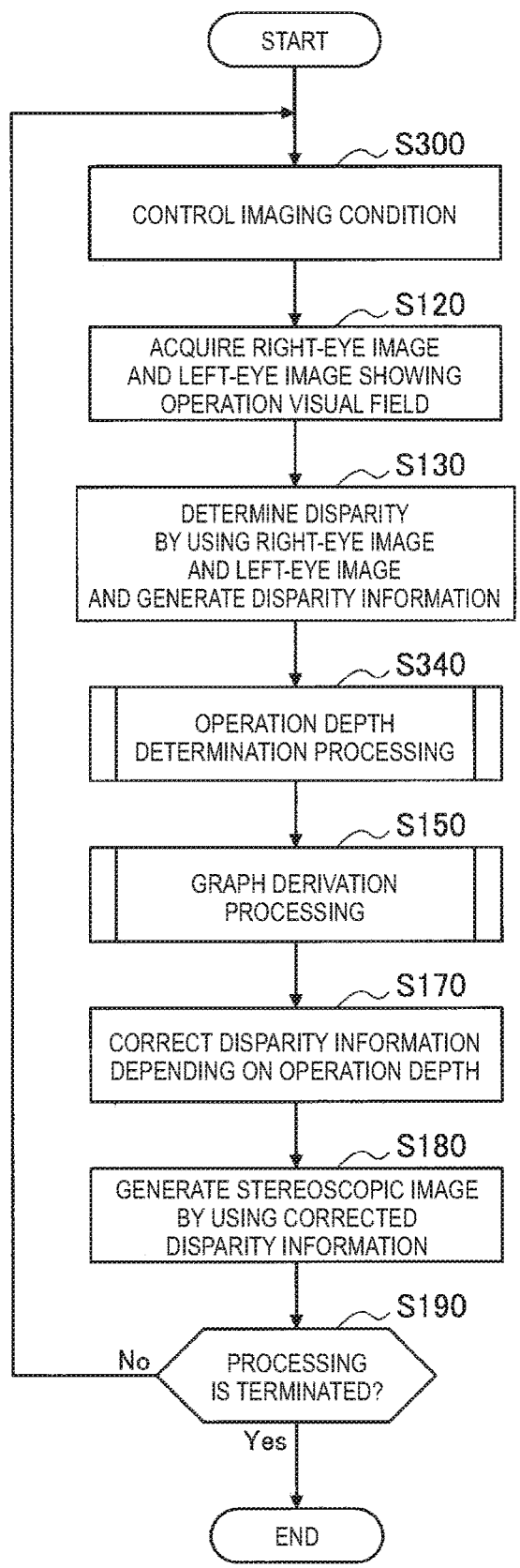
FIG. 17 is a flowchart showing an example of a flow of stereoscopic image generation processing according to the third embodiment.

FIG. 17 is a flowchart showing an example of a flow of stereoscopic image generation processing that can be executed by the CCU 51 according to the third embodiment. When referring to FIG. 17, first, the imaging control unit 310 controls an imaging condition by executing, for example, control functions such as autofocus and exposure control (Step S300). For example, as a result of execution of autofocus, it is possible to determine a focus point position and a focal distance as the imaging condition.

Then, the image acquisition unit 120 acquires a right-eye image and left-eye image showing an operation visual field (Step S120). Then, the disparity determination unit 130 determines a disparity for each pixel position by using the right-eye image and left-eye image acquired by the image acquisition unit 120 and generates disparity information (Step S130).

Then, the depth determination unit 340 executes operation depth determination processing in order to determine an operation depth of medical operation whose image is to be captured (Step S340). An example of a detailed flow of the operation depth determination processing executed herein will be further described below.

Then, the correction unit 150 executes graph derivation processing in order to determine how to correct the disparity information generated by the disparity determination unit 130 depending on the operation depth (Step S150). The graph derivation processing executed herein may be similar to, for example, the processing described with reference to FIGS. 12A to 12C.

Then, the correction unit 150 executes correction of the disparity information depending on the operation depth by using a correction graph (or a correction profile showing a difference between the correction graph and an initial graph) derived as a result of the graph derivation processing (Step S170).

Then, the 3D image generation unit 170 shifts a horizontal position of each pixel of a subject in at least one of the right-eye image and left-eye image acquired by the image acquisition unit 120 by using the disparity information corrected by the correction unit 150, thereby generating a stereoscopic image (Step S180).

Steps S300 to S180 described above are repeated until a termination condition of the stereoscopic image generation processing is satisfied (Step S190). For example, when user input to give an instruction to terminate the processing is detected via the input device 59, the above stereoscopic image generation processing is terminated.

(2) Operation Depth Determination Processing

Figure 18:
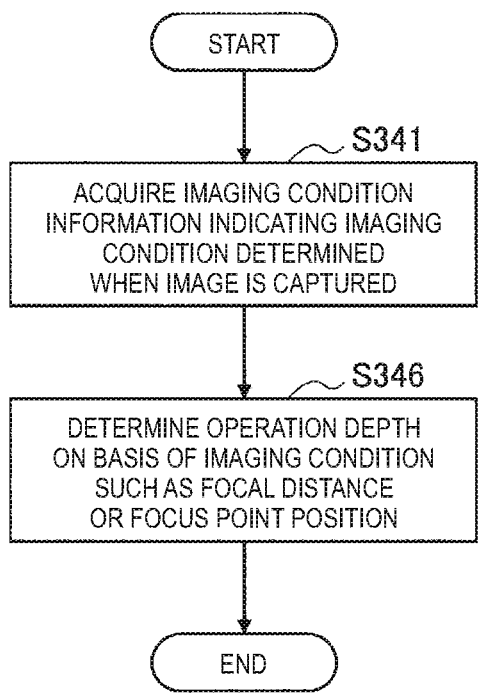
FIG. 18 is a flowchart showing an example of a detailed flow of operation depth determination processing according to the third embodiment.

FIG. 18 is a flowchart showing an example of the detailed flow of the operation depth determination processing shown in FIG. 17. When referring to FIG. 18, first, the depth determination unit 340 acquires imaging condition information indicating the imaging condition determined when the image of the operation visual field has been captured from the imaging control unit 310 (Step S341). Then, the depth determination unit 340 calculates a depth of the subject on the basis of the imaging condition indicated by the acquired imaging condition information, such as a focal distance or a focus point position, and determines that the calculated depth is an operation depth (Step S346).

5. Reduction in Stereoscopic Effect

The above embodiments of the technology according to the present disclosure are applicable not only to emphasis of a stereoscopic effect but also to reduction in the stereoscopic effect that can be performed for the purpose of, for example, reducing a burden on a sight of the user. Reduction in the stereoscopic effect can be achieved by correcting a disparity in a similar way to emphasis of the stereoscopic effect, except that a direction of correction of the disparity (or a sign of the shift amount Δu shown in FIG. 4) is inverted.

Figure 19:
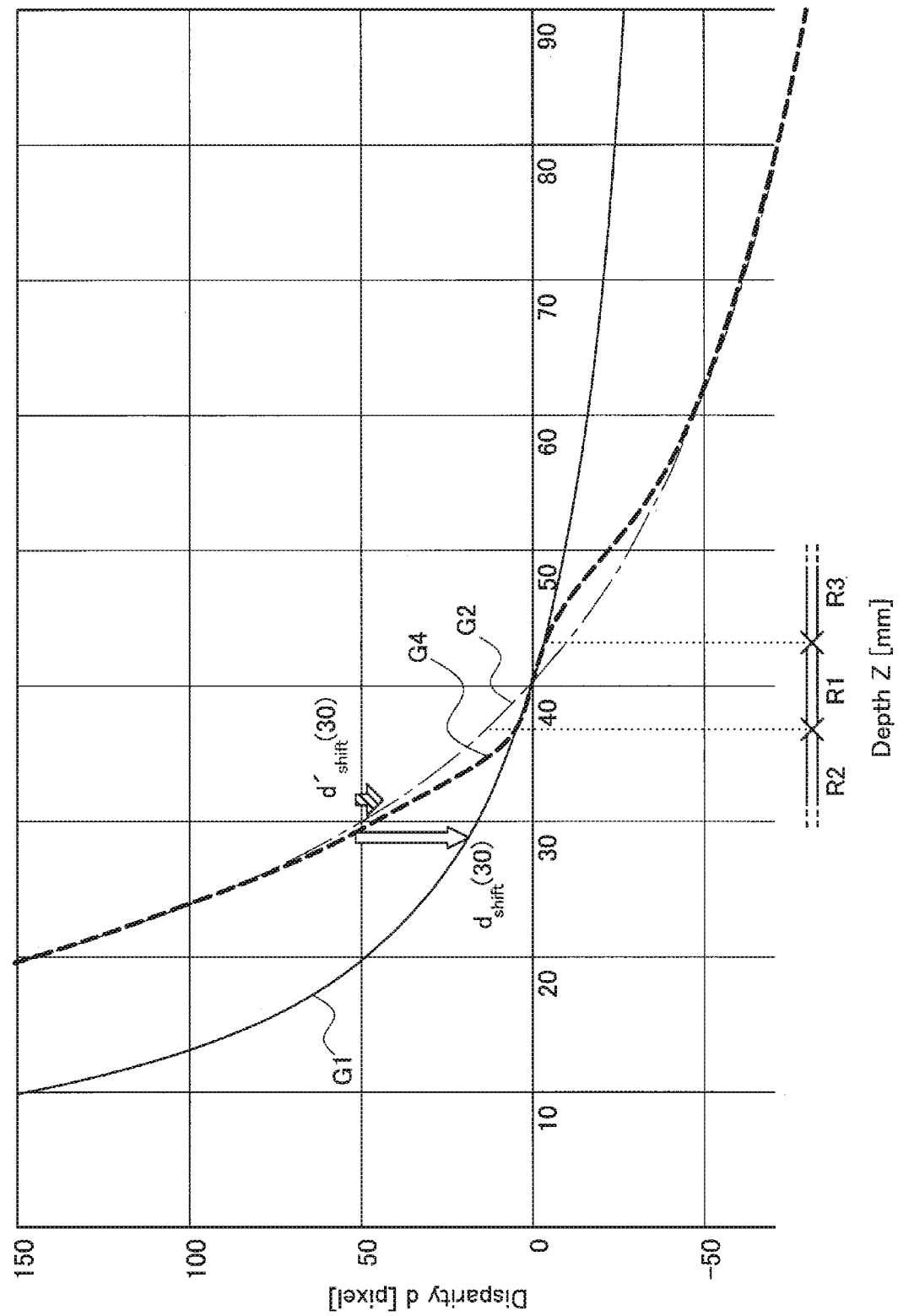
FIG. 19 is an explanatory diagram for describing an example where a correction factor for reducing a stereoscopic effect is reduced depending on an operation depth.

FIG. 19 is an explanatory diagram for describing an example where a correction factor for reducing the stereoscopic effect is reduced depending on an operation depth. FIG. 19 shows the graphs G1 and G2 that have been described with reference to FIG. 5 again. However, although the graph G1 is an initial graph and the graph G2 is an intermediate graph in a case of emphasizing the stereoscopic effect, the graph G2 is an initial graph and the graph G1 is an intermediate graph herein. Further, both the reference depth and the operation depth have 40 mm. For example, in a case of reducing the stereoscopic effect, the CCU 51 derives a correction graph G4 having a track that matches with the intermediate graph G1 within the operation depth range R1 having a small depth difference from the operation depth and is separated from the intermediate graph G1 and approaches the initial graph G2 as the depth difference from the operation depth is increased. According to correction of a disparity using such a correction graph G4, a basic correction factor that reduces an actual base length to a shorter pseudo base length is applied within the operation depth range R1, whereas a correction factor that is relatively reduced from the basic correction factor is applied within the depth ranges R2 and R3 out of the operation depth range R1. For example, a shift amount $d'_{shift}(30)$ at the depth Z=30 mm based on the correction graph G4 is especially smaller than a shift amount $d_{shift}(30)$ that is supposed to be necessary at the depth Z=30 mm in a case where the correction factor is not reduced.

6. Conclusion

Hereinabove, the embodiments of the technology according to the present disclosure have been described in detail with reference to FIGS. 1 to 19. According to the above embodiments, an operation depth of medical operation whose image is to be captured is determined and disparity information indicating a disparity determined by using the captured image is corrected depending on the determined operation depth. This makes it possible to correct the disparity to meet needs in the medical operation, thereby adaptively changing a stereoscopic effect without greatly reducing accuracy of an image to be displayed.

Further, according to the above embodiments, correction of the disparity information is performed to emphasize or reduce a stereoscopic effect of a stereoscopic image generated on the basis of the captured image. Note that, when the correction is performed, a uniform correction factor is not used, and, instead of this, a correction factor of the disparity can be reduced within a second depth range having a large depth difference from an operation depth as compared with a first depth range having a small depth difference from the operation depth. Therefore, it is possible to sufficiently achieve the purpose of emphasizing or reducing the stereoscopic effect at, in particular, an operation depth at which the user makes close observation and in the vicinity of the operation depth by correcting the disparity information and effectively reduce a defect of pixel information within a peripheral range in which such a defect tends to be generated.

Further, according to a certain example, a lower limit of sensitivity of the stereoscopic effect is set within the first depth range having a small depth difference from the operation depth. In this case, it is possible to secure a required minimum stereoscopic effect within an operation depth range in which user operation is mainly performed and help the user to perform accurate operation. Further, according to a certain example, the correction factor of the disparity within the second depth range is reduced so that an index regarding a defect amount of pixel information caused by correction of the disparity satisfies a predetermined condition. In this case, at least a certain level of accuracy is secured in an image whose disparity has been corrected, and the image is prevented from being remarkably failed.

Further, according to a certain example, a basic correction factor determined in accordance with a base length between a right-eye display image and a left-eye display image forming the stereoscopic image is applied within the first depth range, and a correction factor that is relatively reduced from the basic correction factor is applied within the second depth range. In this case, it is possible to give a stereoscopic effect that causes the user to feel as if an actual base length of the stereoscopic image is enlarged (or reduced) to be a desired pseudo base length to the user at an operation depth and in the vicinity thereof, and, at the same time, it is possible to reduce the defect of pixel information.

Further, according to a certain example, the operation depth can be determined on the basis of the type of operation to be performed. In this case, the operation depth is easily set, and, even in a case where the user does not know a value to be set as the operation depth, the system can determine an appropriate operation depth only by the user specifying the type of operation. Further, according to a certain example, the operation depth can be determined on the basis of the type of instrument to be used. Also in this case, the operation depth is easily set. For example, in a case where the same type of instrument is repeatedly used, the system can automatically set the operation depth set once again. In a case where the operation depth is directly input via the user interface, the user can arbitrarily set an optimal operation depth desirable for the user himself/herself.

Further, according to a certain example, the operation depth can be dynamically adjusted on the basis of an image analysis result obtained in a period of time in which an image is captured or an imaging condition. In this case, it is possible to continuously correct the stereoscopic effect within an appropriate operation depth range while following a situation of operation that is changeable over time and reduce the defect of pixel information.

Note that examples of the image processing system including a surgical endoscope have been mainly described in the present specification. However, the technology according to the present disclosure is not limited to such examples and is also applicable to other types of medical observation devices such as a microscope. Further, the technology according to the present disclosure may be achieved as an image processing module (e.g., image processing chip) or camera module to be mounted on such medical observation devices.

The image processing described in the present specification may be achieved by using any one of software, hardware, and a combination of software and hardware. Programs forming software are stored in advance on, for example, a storage medium (non-transitory medium) provided inside or outside each device. In addition, each program is read into a random access memory (RAM) at the time of, for example, execution and is executed by a processor such as a CPU.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical image processing device including:

a depth determination unit configured to determine an operation depth of medical operation whose image is to be captured;

a disparity determination unit configured to determine a disparity by using a captured image showing a visual field observed in the operation and generate disparity information; and a correction unit configured to correct the disparity information depending on the operation depth determined by the depth determination unit.

(2)

The medical image processing device according to (1), in which the correction unit corrects the disparity information so as to emphasize a stereoscopic effect expressed by a stereoscopic image generated on a basis of the captured image.

(3)

The medical image processing device according to (2), in which the correction unit reduces a correction factor of the disparity within a second depth range having a large depth difference from the operation depth as compared with a first depth range having a small depth difference from the operation depth.

(4)

The medical image processing device according to (3), in which a lower limit of sensitivity of the stereoscopic effect is set within the first depth range, and the lower limit is not set within the second depth range.

(5)

The medical image processing device according to (3) or (4), in which the correction unit reduces the correction factor of the disparity within the second depth range so that an index regarding a defect amount of pixel information caused by correction of the disparity does not exceed an allowable upper limit.

(6)

The medical image processing device according to any one of (1) to (5), in which the depth determination unit determines the operation depth on a basis of a type of the operation.

(7)

The medical image processing device according to any one of (1) to (6), in which the depth determination unit determines the operation depth on a basis of a type of instrument to be used in the operation.

(8)

The medical image processing device according to any one of (1) to (7), in which the depth determination unit determines the operation depth on a basis of user input acquired via a user interface.

(9)

The medical image processing device according to any one of (1) to (5), in which the depth determination unit determines the operation depth on a basis of analysis of the captured image.

(10)

The medical image processing device according to any one of (1) to (5), in which the depth determination unit determines the operation depth on a basis of an imaging condition to be determined when an image of the visual field is captured.

(11)

The medical image processing device according to any one of (1) to (10), in which the captured image includes a right-eye image and a left-eye image, and the correction unit applies a basic correction factor determined in accordance with a base length between the right-eye image and the left-eye image within the first depth range and applies a correction factor that is relatively reduced from the basic correction factor within the second depth range.

(12)

The medical image processing device according to (5), further including a setting unit configured to provide a user interface that allows the user to set the allowable upper limit of the index regarding the defect amount of pixel information.

(13)

The medical image processing device according to any one of (1) to (12), in which the operation includes surgery.

(14)

The medical image processing device according to any one of (1) to (13), in which the captured image is acquired via an image sensor included in a camera head of a medical endoscope.

(15)

The medical image processing device according to any one of (1) to (14), further including a generation unit configured to generate a stereoscopic image on a basis of the captured image by using the disparity information corrected by the correction unit.

(16)

The medical image processing device according to (1), in which the correction unit corrects the disparity information so as to reduce a stereoscopic effect expressed by a stereoscopic image generated on a basis of the captured image.

(17)

The medical image processing device according to (16), in which the correction unit reduces a correction factor of the disparity within a second depth range having a large depth difference from the operation depth as compared with a first depth range having a small depth difference from the operation depth.

(18)

A medical image processing system including:

the medical image processing device according to any one of (1) to (17); and an imaging device configured to capture an image of the visual field and generate the captured image.

(19)

An image processing method executed by a medical image processing device, the image processing method including:

determining an operation depth of medical operation whose image is to be captured;

determining a disparity by using a captured image showing a visual field observed in the operation and generating disparity information; and correcting the disparity information depending on the determined operation depth.

(20)

A program for causing a processor that controls a medical image processing device to function as:

a depth determination unit configured to determine an operation depth of medical operation whose image is to be captured;

a disparity determination unit configured to determine a disparity by using a captured image showing a visual field observed in the operation and generate disparity information; and a correction unit configured to correct the disparity information depending on the operation depth determined by the depth determination unit.

REFERENCE SIGNS LIST 1 medical image processing system
13 camera head (imaging device)
51 CCU (image processing device)
53 monitor (display device)
110, 310 imaging control unit
120, 220 image acquisition unit
130 disparity determination unit
140, 240, 340 depth determination unit
150 correction unit
160, 260 storage unit
170 3D image generation unit
180, 280 setting unit

The invention claimed is:

1. A medical image processing device comprising:
circuitry configured to:
determine an operation depth of a medical operation whose image is to be captured;
determine a disparity by using a captured image showing a visual field observed in the medical operation and generate disparity information; and
correct the disparity information depending on the determined operation depth, wherein
the correction of the disparity information emphasizes a stereoscopic effect expressed by a stereoscopic image generated on a basis of the captured image and reduces a correction factor of the disparity within a second depth range having a large depth difference from the operation depth as compared with a first depth range having a small depth difference from the operation depth.

2. The medical image processing device according to claim 1, wherein
a lower limit of sensitivity of the stereoscopic effect is set within the first depth range, and the lower limit is not set within the second depth range.

3. The medical image processing device according to claim 1, wherein
the circuitry configured to correct the disparity information is further configured to reduce the correction factor of the disparity within the second depth range so that an index regarding a defect amount of pixel information caused by correction of the disparity does not exceed an allowable upper limit.

4. The medical image processing device according to claim 1, wherein
the circuitry configured to determine the operation depth determines the operation depth on a basis of a type of the medical operation.

5. The medical image processing device according to claim 1, wherein
the circuitry configured to determine the operation depth determines the operation depth on a basis of a type of instrument to be used in the medical operation.

6. The medical image processing device according to claim 1, wherein
the circuitry configured to determine the operation depth determines the operation depth on a basis of user input acquired via a user interface.

7. The medical image processing device according to claim 1, wherein
the circuitry configured to determine the operation depth determines the operation depth on a basis of analysis of the captured image.

8. The medical image processing device according to claim 1, wherein
the circuitry configured to determine the operation depth determines the operation depth on a basis of an imaging condition to be determined when an image of the visual field is captured.

9. The medical image processing device according to claim 1, wherein
the captured image includes a right-eye image and a left-eye image, and
the circuitry configured to correct the disparity information is further configured to apply a basic correction factor determined in accordance with a base length between the right-eye image and the left-eye image within the first depth range and applies a correction factor that is relatively reduced from the basic correction factor within the second depth range.

10. The medical image processing device according to claim 3, wherein the circuitry is further configured to provide a user interface that allows the user to set the allowable upper limit of the index regarding the defect amount of pixel information.

11. The medical image processing device according to claim 1, wherein
the medical operation includes surgery.

12. The medical image processing device according to claim 1, wherein
the captured image is acquired via an image sensor included in a camera head of a medical endoscope.

13. The medical image processing device according to claim 1, wherein the circuitry is further configured to generate a stereoscopic image on a basis of the captured image by using the disparity information corrected by the circuitry configured to correct the disparity information.

14. A medical image processing device comprising circuitry configured to:
determine an operation depth of a medical operation whose image is to be captured;
determine a disparity by using a captured image showing a visual field observed in the medical operation and generate disparity information; and
correct the disparity information depending on the determined operation depth, wherein the correction of the disparity information corrects the disparity information so as to reduce a stereoscopic effect expressed by a stereoscopic image generated on a basis of the captured image and wherein the correction of the disparity information reduces a correction factor of the disparity within a second depth range having a large depth difference from the operation depth as compared with a first depth range having a small depth difference from the operation depth.

15. A medical image processing system comprising:
the medical image processing device according to claim 1; and
an imaging sensor configured to capture an image of the visual field and generate the captured image.

16. An image processing method executed by a medical image processing device, the image processing method comprising:
determining, using circuitry, an operation depth of medical operation whose image is to be captured;
determining, using the circuitry, a disparity by using a captured image showing a visual field observed in the operation and generating disparity information; and
correcting, using the circuitry, the disparity information depending on the determined operation depth, wherein
the correcting corrects the disparity information so as to emphasize a stereoscopic effect expressed by a stereoscopic image generated on a basis of the captured image, and
the correcting reduces a correction factor of the disparity within a second depth range having a large depth difference from the operation depth as compared with a first depth range having a small depth difference from the operation depth.

17. A non-transitory computer readable medium including executable instructions, which when executed by a computer cause the computer to:
determine an operation depth of a medical operation whose image is to be captured;
determine a disparity by using a captured image showing a visual field observed in the medical operation and generate disparity information; and
correct the disparity information depending on the determined operation depth, wherein
the correction of the disparity information emphasizes a stereoscopic effect expressed by a stereoscopic image generated on a basis of the captured image and reduces a correction factor of the disparity within a second depth range having a large depth difference from the operation depth as compared with a first depth range having a small depth difference from the operation depth.

* * * * *